(12) United States Patent
Katsurada et al.

(10) Patent No.: US 11,874,455 B2
(45) Date of Patent: Jan. 16, 2024

(54) LIGHT IRRADIATION DEVICE AND LIGHT IRRADIATION SYSTEM

(71) Applicant: ASAHI INTECC CO., LTD., Seto (JP)

(72) Inventors: Yuko Katsurada, Seto (JP); Toshihiko Tsukamoto, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 0 days.

(21) Appl. No.: 17/714,637

(22) Filed: Apr. 6, 2022

(65) Prior Publication Data
US 2022/0229282 A1 Jul. 21, 2022

Related U.S. Application Data

(63) Continuation of application No. PCT/JP2020/030964, filed on Aug. 17, 2020.

(30) Foreign Application Priority Data

Oct. 17, 2019 (JP) .................................. 2019-190447

(51) Int. Cl.
*F21V 8/00* (2006.01)
*G02B 23/24* (2006.01)
*A61N 5/06* (2006.01)

(52) U.S. Cl.
CPC ....... *G02B 23/2469* (2013.01); *G02B 6/0008* (2013.01); *A61N 5/0601* (2013.01); *A61N 5/062* (2013.01); *A61N 2005/063* (2013.01)

(58) Field of Classification Search
CPC .......................... G02B 23/2469; G02B 6/0008
See application file for complete search history.

(56) References Cited

U.S. PATENT DOCUMENTS 3,123,066 A 3/1964 Brumley
4,669,467 A * 6/1987 Willett ................. G02B 6/4296
606/7

(Continued)

FOREIGN PATENT DOCUMENTS

JP 2001037892 A 2/2001
JP 2007528752 A 10/2007

(Continued)

OTHER PUBLICATIONS

Makoto Mitsunaga, et al., "Cancer Cell-Selective In Vivo Near Infrared Photoimmunotherapy Targeting Specific Membrane Molecules," Nature Medicine 2012 (year of publication sufficiently early that month is not at issue) 17(12), pp. 1685-1691.

(Continued)

*Primary Examiner* — Evan P Dzierzynski
(74) *Attorney, Agent, or Firm* — Oliff PLC

(57) ABSTRACT

A light irradiation device having an elongated outer shape includes: an optical fiber for emitting light from its distal end, which has a curved part, in which the distal end is oriented in a direction intersecting with a longitudinal direction of the light irradiation device by the curved part; and a light transmitting holder that retains a shape of the curved part of the optical fiber. The optical fiber has a core, or has the core and an outer surface layer, and the holder has a refractive index smaller than a refractive index of the core or a refractive index of the outer surface layer of the optical fiber.

20 Claims, 17 Drawing Sheets

(56) References Cited

U.S. PATENT DOCUMENTS

| | | | | |
|---|---|---|---|---|
| 4,747,405 A * | 5/1988 | Leckrone | ............... | A61B 18/20 606/7 |
| 4,852,567 A * | 8/1989 | Sinofsky | .............. | A61B 18/245 606/7 |
| 5,129,897 A * | 7/1992 | Daikuzono | ............ | A61B 18/22 606/16 |
| 5,495,541 A | 2/1996 | Murray et al. | | |
| 6,530,921 B1 | 3/2003 | Maki | | |
| 6,607,526 B1 * | 8/2003 | Maki | .................... | A61N 5/0601 600/101 |
| 2002/0002370 A1 * | 1/2002 | Levatter | ............... | A61B 18/245 606/15 |
| 2018/0008122 A1 | 1/2018 | Arai et al. | | |

FOREIGN PATENT DOCUMENTS

| | | | |
|---|---|---|---|
| JP | 2009533078 A | 9/2009 |
| JP | 2014523907 A | 9/2014 |
| JP | 2018000867 A | 1/2018 |
| WO | 2005007216 A2 | 1/2005 |
| WO | 2007109204 A1 | 9/2007 |
| WO | 2013009475 A1 | 1/2013 |

OTHER PUBLICATIONS

Kazuhide Sato, et al., "Spatially selective depletion of tumor-associated regulatory T cells with near-infrared photoimmunotherapy," Science Translational Medicine 2016 (year of publication sufficiently early that month is not at issue) vol. 8 Issue 352, ra110.

Shuhei Okuyama, et al., "Interstitial near-infrared photoimmunotherapy: effective treatment areas and light doses heeded for use with fiber optic diffusers," Oncotarget Feb. 2018. 16; 9(13), pp. 11159-11169.

* cited by examiner

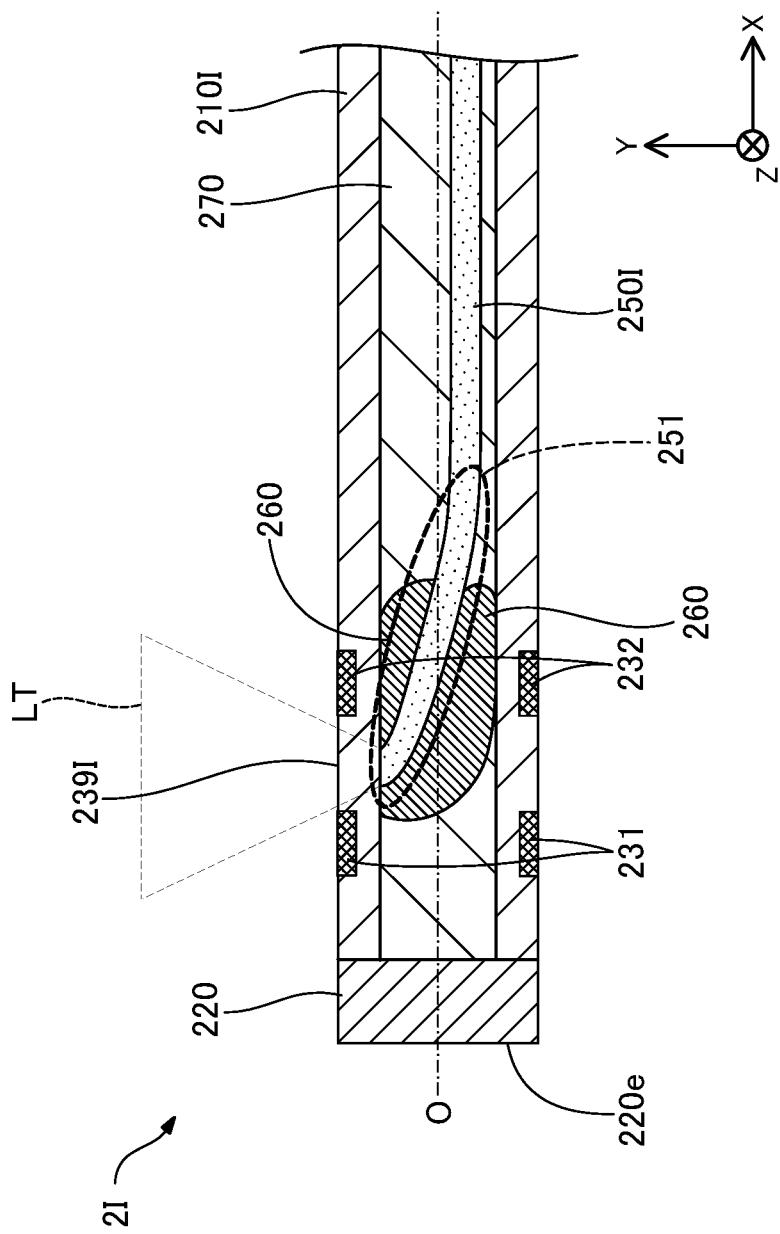

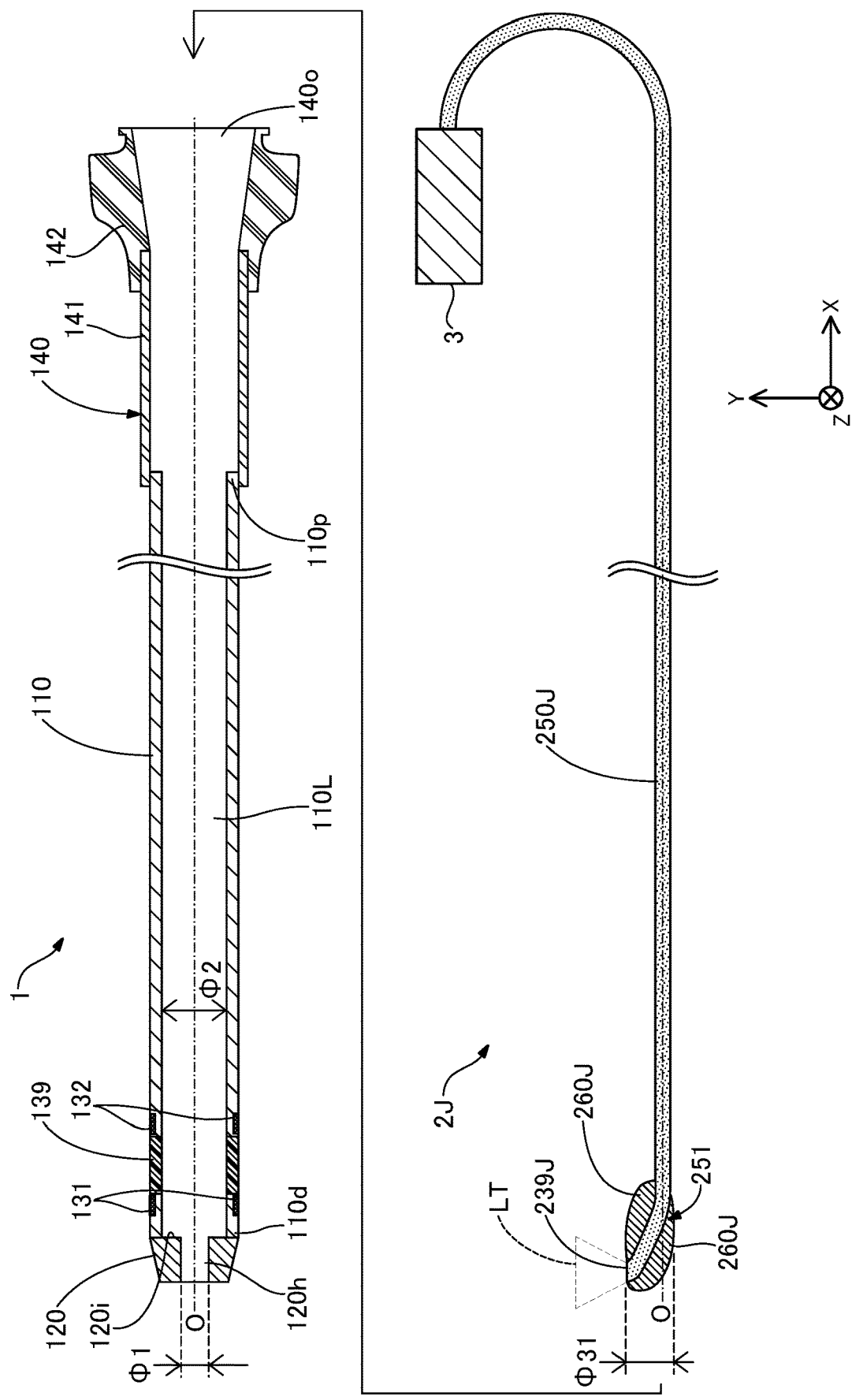

LIGHT IRRADIATION DEVICE AND LIGHT IRRADIATION SYSTEM

CROSS REFERENCE TO RELATED APPLICATIONS

The present application is a Bypass Continuation of International Application No. PCT/JP2020/030964, filed on Aug. 17, 2020, which claims priority to Japanese Patent Application No. 2019-190447, filed on Oct. 17, 2019. The contents of these applications are incorporated herein by reference in their entirety.

TECHNICAL FIELD

The disclosed embodiments relate to a light irradiation device and a light irradiation system.

BACKGROUND ART

In cancer treatment, surgical, radiological, and pharmacological (chemical) methods are used alone or in combination, and development of each of these techniques is progressing in recent years. However, there are many cancers for which a satisfactory treatment technique has not yet been found, and further development of the treatment techniques is expected. A method called photodynamic therapy (PDT) is known as one of these cancer treatment techniques. In PDT, a photosensitizer is administered intravenously and then irradiated with light, to generate reactive oxygen in cancer cells and kill the cancer cells (see, for example, Non-Patent Literature 1). However, in PDT, the photosensitizer is accumulated with low selectivity in the cancer cells, so that the magnitude of the side effects caused by the uptake of the photosensitizer into normal cells is an issue and thus, PDT is not widely used as a treatment technique.

Therefore, a treatment technique that is attracting attention in recent years is near-infrared photoimmunotherapy (NIR-PIT). NIR-PIT uses a conjugate in which two compounds, an antibody against a specific antigen of cancer cells and a photosensitizer (for example, IRDye 700DX), are bound. When administered intravenously, this conjugate selectively accumulates in cancer cells in the body. Subsequently, if irradiation with light having an excitation wavelength (for example, 690 nm) of the photosensitizer in the conjugate is performed, the conjugate is activated and exhibits an anticancer effect (see, for example, Patent Literature 1). Selective accumulation of antibodies in the cancer and local light irradiation in NIR-PIT allow for reduction of side effects compared to PDT. Further, in NIR-PIT, irradiation with light in the near-infrared region of 690 nm (NIR irradiation) is performed, for example, and thus, an effect of the NIR irradiation on the immune system can also be expected (see, for example, Non-Patent Literature 2).

A certain wavelength region including the 690 nm region of the example described above is also called a spectroscopic window of a living body. Although light in this wavelength region is absorbed less by biological components than light in other wavelength regions, the light does not sufficiently penetrate when light irradiation is performed from the body surface, and thus, there is a problem in that NIR-PIT cannot be applied to cancers deep inside the body. Therefore, in recent years, research is being conducted on NIR-PIT in which light irradiation is performed at a position closer to the cancer cells, instead of light irradiation from the body surface (see, for example, Non-Patent Literature 3). For example, Patent Literature 2 to Patent Literature 4 disclose devices that can be used in such PDT and NIR-PIT. All of the devices described in Patent Literature 2 to Patent Literature 4 are inserted into a living body lumen such as blood vessel to be used, so that the deep inside of the body can be irradiated with a light transmitted by an optical fiber. Also, in the device described in Patent Literature 5, a wound is caused with a laser light in body tissues.

CITATION LIST

Patent Literature

Patent Literature 1: JP 2014-523907 W
Patent Literature 2: JP 2018-000867 A
Patent Literature 3: JP 2007-528752 W
Patent Literature 4: JP 2001-037892 A
Patent Literature 5: JP 2009-533078 W

Non-Patent Literature

Non-Patent Literature 1: Makoto Mitsunaga, Mikako Ogawa, Nobuyuki Kosaka Lauren T. Rosenblum, Peter L. Choyke, and Hisataka Kobayashi, Cancer Cell-Selective In Vivo Near Infrared Photoimmunotherapy Targeting Specific Membrane Molecules, Nature Medicine 2012 17(12): p. 1685-1691

Non-Patent Literature 2: Kazuhide Sato, Noriko Sato, Biying Xu, Yuko Nakamura, Tadanobu Nagaya, Peter L. Choyke, Yoshinori Hasegawa, and Hisataka Kobayashi, Spatially selective depletion of tumor-associated regulatory T cells with near-infrared photoimmunotherapy, Science Translational Medicine 2016 Vol. 8 Issue 352, ra110

Non-Patent Literature 3: Shuhei Okuyama, Tadanobu Nagaya, Kazuhide Sato, Fusa Ogata, Yasuhiro Maruoka, Peter L. Choyke, and Hisataka Kobayashi, Interstitial near-infrared photoimmunotherapy: effective treatment areas and light doses needed for use with fiber optic diffusers, Oncotarget 2018 Feb. 16; 9(13): p. 11159-11169

SUMMARY

Technical Problem

Herein, an optical fiber generally transmits light by total light reflection using a difference in refractive index between a core and a clad covering an outer peripheral surface of the core, and emits light from the core exposed on a distal end of the optical fiber. On the other hand, in a device that is used so as to be inserted into a living body lumen to irradiate a deep inside of the body with light, a direction of the light irradiation is preferably a direction of tissues surrounding the living body lumen, i.e. a direction intersecting with a long axial direction of the device. In this regard, the devices described in Patent Literature 4 and Patent Literature 5 include a guide means (guide member), and the optical fiber is moved using the guide means, so that the distal end of the optical fiber can be oriented in a direction intersecting with the long axial direction of the device. However, the techniques described in Patent Literature 4 and Patent Literature 5 have had a problem that the device has a complicated structure and an increased diameter. In addition, for the devices described in Patent Literature 2 and Patent Literature 3, the light irradiation in the direction intersecting with the long axial direction of the device is not taken into consideration.

It is noted that this problem is not limited to PDT and NIR-PIT, and is common to all devices used in examinations or treatments including a light irradiation process in the body. Further, such a problem is not limited to devices to be inserted into a blood vessel, and is common to all devices to be inserted into living body lumens, such as a vascular system, a lymphatic system, a biliary system, a urinary system, a respiratory system, a digestive system, a secretory gland, and a reproductive organ.

The disclosed embodiments have been contrived to solve at least a part of the above-mentioned problems, and an object of the disclosed embodiments is to decrease a diameter of a device that can emit light from an optical fiber in a direction intersecting with a long axial direction of the device.

Solution to Problem

The disclosed embodiments have been made to solve at least a part of the above-described problems, and can be implemented as the following aspects.

(1) According to one aspect of the disclosed embodiments, a light irradiation device having an elongated outer shape is provided. The light irradiation device includes: an optical fiber that emits a light from its distal end and includes a curved part, in which the curved part orients the distal end in a direction intersecting with a long axial direction of the light irradiation device; a light transmitting holding member that retains a shape of the curved part of the optical fiber. The optical fiber includes a core, or the optical fiber includes the core and one or more covering layers, and the holding member has a refractive index lower than of a member constituting an outer surface of the optical fiber.

According to this configuration, while the distal end of the optical fiber is oriented in the direction intersecting the long axial direction of the light irradiation device by the curved part, the shape of the curved part is retained by the holding member. Thereby, movement of the optical fiber by using a guide means simplifies the configuration of the light irradiation device compared to a configuration in which the distal end of the optical fiber is oriented in a direction intersecting with the long axial direction of the light irradiation device, so that the diameter of the light irradiation device can be decreased. In addition, the holding member has a refractive index lower than of the member constituting the outer surface of the optical fiber. Thus, the light inside the optical fiber can be reflected at a boundary between the member constituting the outer surface of the optical fiber and the holding member e.g. compared to a case where the shape of the curved part is retained using a holding member having a refractive index equivalent to or higher than that of the member constituting the outer surface of the optical fiber. As a result, the light irradiation device having this configuration makes it possible to reduce light leakage from the inside of the optical fiber.

(2) In the light irradiation device according to the aspect described above, the holding member may be arranged at least adjacent to an inner peripheral side of the curved part.

According to this configuration, the shape of the curved part of the optical fiber can be retained at least from the inner peripheral side of the curved part. The inner peripheral side of the curved part is, in other words, a direction in which the distal end of the optical fiber is oriented, i.e. a direction in which the light is emitted from the optical fiber. Herein, in general, the material for forming the holding member has a refractive index higher than of air. Thus, for example, the light leakage in the direction not for the light emission from the optical fiber can be further reduced, by leaving a void on the outer peripheral side (direction in which the light is not emitted from the optical fiber) of the curved part without disposing the holding member.

(3) In the light irradiation device according to the aspects described above, the holding member includes an inner holding member arranged adjacent to the inner peripheral side of the curved part and an outer holding member arranged adjacent to the outer peripheral side of the curved part, and the outer holding member may have a refractive index lower than of the inner holding member.

According to this configuration, the shape of the curved part can be firmly retained from different directions of the inner peripheral side and the outer peripheral side of the curved part. The outer holding member disposed on the outer peripheral side of the curved part has a refractive index lower than of the inner holding member disposed on the inner peripheral side of the curved part. Thus, the light leakage from the outer holding member arranged in the direction not for the light emission from the optical fiber can be more reduced compared to the light leakage from the inner holding member arranged in the direction of the light emission from the optical fiber.

(4) In the light irradiation device according to the aspects described above, the inner holding member includes a first inner holding member disposed on the distal end side and a second inner holding member disposed on the proximal end side, and the second inner holding member may have a refractive index lower than of the first inner holding member and higher than of the outer holding member.

According to this configuration, since the inner holding member includes the first inner holding member disposed on the distal end side and the second inner holding member disposed on the proximal end side, a degree of the light leakage can be changed by controlling the refractive indices of the first and second inner holding members. The second inner holding member has a refractive index lower than of the first inner holding member and higher than of the outer holding member. Thus, the light leakage from the outer holding member arranged in the direction not for the light emission from the optical fiber can be more reduced compared to the light leakage from the first and second inner holding members arranged in the direction of the light emission from the optical fiber. Furthermore, the light leakage from the second inner holding member disposed on the proximal end side can be more reduced compared to the light leakage from the first inner holding member disposed on the distal end side.

(5) The light irradiation device according to the aspects described above further includes a hollow shaft accommodating the optical fiber and the holding member, wherein the proximal end side with respect to the holding member within the hollow shaft may be filled with a resin member having a refractive index lower than of the holding member.

According to this configuration, since the proximal end side with respect to the holding member within the hollow shaft is filled with the resin member, the elongated shape of the light irradiation device can be maintained. In addition, since the resin member has the refractive index lower than of the holding member, the light leakage can be reduced via the resin member.

(6) In the light irradiation device according to the aspects described above, a part on the distal end side of the curved part protrudes from the distal end of the hollow shaft, and the holding member may cover the periphery of the curved part protruding from the hollow shaft.

According to this configuration, a part on the distal end side of the curved part, i.e. the distal end of the optical fiber is protruded from the distal end of the hollow shaft, so that the light emitted from the distal end of the optical fiber can be prevented from being blocked by the hollow shaft. In addition, since the holding member covers the periphery of the protruding curved part, the periphery of the protruding curved part can be protected.

(7) The light irradiation device according to the aspects described above further includes the hollow shaft accommodating the optical fiber and the holding member, wherein a part on the distal end side of the curved part protrudes from the distal end of the hollow shaft, and the holding member may cover the periphery of the curved part protruding from the hollow shaft and have substantially the same outer diameter as of the hollow shaft so as to be joined to the distal end of the hollow shaft.

According to this configuration, a part on the distal end side of the curved part, i.e. the distal end of the optical fiber is protruded from the distal end of the hollow shaft, so that the light emitted from the distal end of the optical fiber can be prevented from being blocked by the hollow shaft. In addition, since the holding member covers the periphery of the protruding curved part, the periphery of the protruding curved part can be protected.

(8) According to an aspect of the disclosed embodiments, a light irradiation system is provided. This light irradiation system includes the light irradiation device according to the aspects described above, an elongated tubular catheter into which the light irradiation device is inserted, wherein the catheter has a light transmitting portion for transmitting the inside light to the outside, at a position corresponding to the distal end of the optical fiber in inserting the light irradiation device into the catheter.

According to this configuration, the light irradiation system includes separately the light irradiation device, and the catheter having a light transmitting portion for transmitting the inside light to the outside, at a position corresponding to the distal end of the optical fiber, and therefore the degree of freedom in designing the device can be improved and the range of procedures can be expanded.

It is noted that the disclosed embodiments can be realized in various aspects, for example, the disclosed embodiments can be realized in aspects such as a catheter, a light irradiation device, a light irradiation system in which the catheter and the light irradiation device are provided separately or integrally, and a manufacturing method of the catheter, the light irradiation device, and the light irradiation system.

BRIEF DESCRIPTION OF DRAWINGS

FIG. 16 is an explanatory diagram illustrating a configuration of a light irradiation device according to the tenth embodiment.

FIG. 17 is an explanatory diagram illustrating a configuration of a light irradiation system according to the eleventh embodiment.

DETAILED DESCRIPTION OF EMBODIMENTS

First Embodiment

Figure 1:
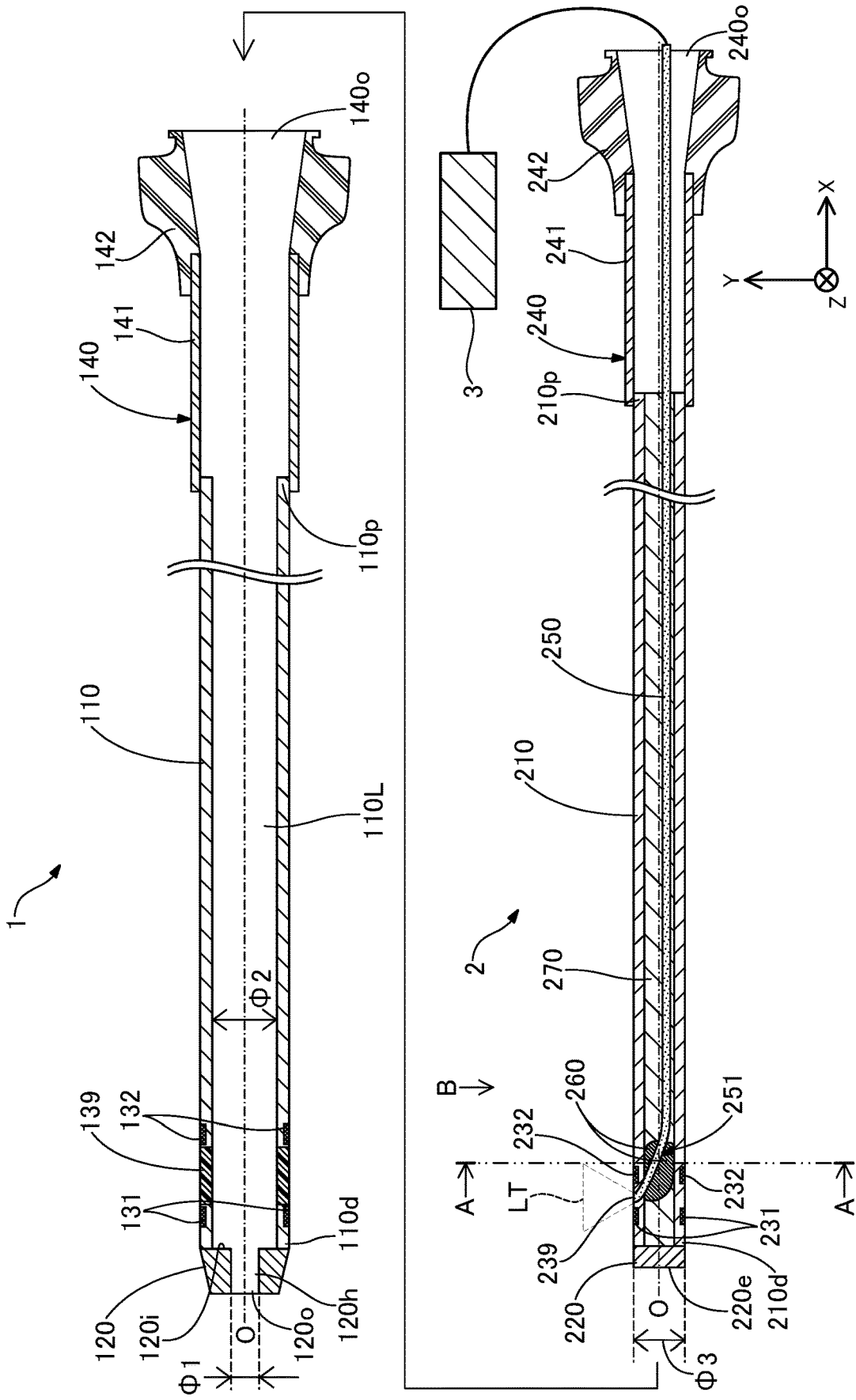
FIG. 1 is an explanatory diagram illustrating a configuration of a light irradiation system according to the first embodiment.

FIG. 1 is an explanatory diagram illustrating a configuration of a light irradiation system according to the first embodiment. The light irradiation system is inserted into a living body lumen such as a vascular system, a lymphatic system, a biliary system, a urinary system, a respiratory system, a digestive system, a secretory gland, and a reproductive organ to be used. The light irradiation system emits a light transmitted through an optical fiber, from the living body lumen toward living tissues. The light irradiation system can be used in photodynamic therapy (PDT) and near-infrared photoimmunotherapy (NIR-PIT), for example. The light irradiation system includes a catheter 1 and a light irradiation device 2 that is inserted into the catheter 1 to be used. In FIG. 1, the catheter 1 and the light irradiation device 2 are illustrated separately.

In FIG. 1, an axis passing through a center of the catheter 1 and an axis passing through a center of the light irradiation device 2 are represented by an axis O (dash-dot-dash line). Hereinafter, in a state where the light irradiation device 2 is inserted into the catheter 1, it is assumed that axes passing through the centers of the light irradiation device 2 and the catheter 1 coincide with the axis O, but the axes passing through the centers of the light irradiation device 2 and the catheter 1 when the light irradiation device 2 is inserted into the catheter 1 may be different from each other. Further, in FIG. 1, an X-axis, a Y-axis, and a Z-axis that are orthogonal to each other are illustrated. The X-axis corresponds to a long axial direction (axis O direction) of the catheter 1 and the light irradiation device 2, the Y-axis corresponds to a height direction of the catheter 1 and the light irradiation device 2, and the Z-axis corresponds to a width direction of the catheter 1 and the light irradiation device 2. Hereinafter, the left side (a −X-axis direction) in FIG. 1 is referred to as a "distal end side" of the catheter 1, the light irradiation device 2, and each constitution component, and the right side (a +X-axis direction) in FIG. 1 is referred to as a "proximal end side" of the catheter 1, the light irradiation device 2, and each constitution component. End portions of the catheter 1, the light irradiation device 2, and each constitution component located on the distal end side are referred to as a "distal end", and the distal end and a vicinity thereof are referred to as a "distal end portion". In addition, an end portion located on the proximal end side is referred to as a "proximal end", and the proximal end and the vicinity thereof are referred to as a "proximal end portion". The distal end side corresponds to a "distal side" inserted into a living body, and the proximal end side corresponds to a "proximal side" operated by an operator such as a doctor. These features are common to each drawing after FIG. 1 illustrating an overall configuration.

The catheter 1 has an elongated tube shape and includes a shaft 110, a distal tip 120, and a connector 140. The shaft 110 is an elongated member extending along the axis O. The shaft 110 has a substantially hollow cylindrical (tubular) shape and both ends of the shaft 110, i.e., a distal end portion 110d and a proximal end portion 110p, are open. The shaft 110 includes a lumen 110L inside the shaft 110. The lumen 110L functions as a guide wire lumen for inserting a guide wire through the catheter 1 during delivery of the catheter 1. The lumen 110L functions as a device lumen for inserting the light irradiation device 2 into the catheter 1 after the delivery of the catheter 1. Using a single lumen as both the guide wire lumen and the device lumen, as described above, makes it possible to reduce the diameter of the catheter 1. The shaft 110 may have any outer diameter, inner diameter, and length.

The distal tip 120 is a member that is joined to the distal end portion of the shaft 110 and advances in a living body lumen ahead of other members. As illustrated in FIG. 1, to facilitate the progress of the catheter 1 in the living body lumen, the distal tip 120 has an outer shape with a diameter that decreases from the proximal end side to the distal end side. A through-hole 120h penetrating the distal tip 120 in a direction of the axis O is formed in a substantially central part of the distal tip 120. Here, an opening diameter $\Phi 1$ of the through-hole 120h is smaller than an inner diameter $\Phi 2$ of the lumen 110L of the shaft 110. Therefore, as illustrated in FIG. 1, at a boundary between the shaft 110 and the distal tip 120, an inner surface 120i of the distal tip 120 protrudes and forms a step. An opening 120o of the distal tip 120 leads to the through-hole 120h and is used when inserting a guide wire (not illustrated) into the catheter 1. The distal tip 120 may have any outer diameter and length.

The connector 140 is a member arranged on the proximal end side of the catheter 1 and gripped by the operator. The connector 140 includes a connection portion 141 having a substantially cylindrical shape and a pair of blades 142. A distal end portion of the connection portion 141 is joined to the proximal end portion 110p of the shaft 110, and a proximal end portion of the connection portion 141 is joined to the blades 142. The blades 142 may have a structure that is integrally formed with the connector 140. An opening 140o of the connector 140 leads to the lumen 110L via the inside of the connector 140, and is used when inserting the light irradiation device 2 into the catheter 1. The connection portion 141 may have any outer diameter, inner diameter, and length, and the blades 142 may have any shape.

The shaft 110 of the catheter 1 is further provided with a light transmitting portion 139 and first marker portions 131 and 132. The light transmitting portion 139 transmits light inside the shaft 110 to the outside. The light transmitting portion 139 is a hollow member having a substantially cylindrical shape, an outer diameter that is substantially the same as the outer diameter of the shaft 110, and an inner diameter that is substantially the same as the inner diameter $\Phi 2$ of the lumen 110L of the shaft 110. In other words, the light transmitting portion 139 is provided wholly in the circumferential direction, and wholly transmits light inside the shaft 110 to the outside in the circumferential direction. The light transmitting portion 139 is joined to the shaft 110 at each of the proximal end side and the distal end side. The light transmitting portion 139 can be formed of a transparent resin material having light-transmitting properties, such as an acrylic resin, polyethylene terephthalate, and polyvinyl chloride.

The first marker portions 131 and 132 function as marks indicating positions of the light transmitting portion 139. The first marker portion 131 is provided close to the distal end portion of the light transmitting portion 139, and functions as a mark indicating a position of the distal end portion of the light transmitting portion 139. The first marker portion 132 is provided close to the proximal end portion of the light transmitting portion 139, and functions as a mark indicating a position of the proximal end portion of the light transmitting portion 139. The first marker portions 131 and 132 are hollow members each having a substantially cylindrical shape. In the example of FIG. 1, the first marker portions 131 and 132 are respectively arranged in recess portions formed in an outer surface of the shaft 110 and are joined to the outer surface of the shaft 110. In other words, the first marker portions 131 and 132 are each embedded in the outer surface of the shaft 110 to surround the shaft 110 in the circumferential direction. It is noted that the first marker portions 131 and 132 may be joined to the outer surface of the shaft 110 without the recess portions, and may protrude from the outer surface of the shaft 110. At least one of the first marker portions 131 and 132 may be omitted.

The light irradiation device 2 has an elongated outer shape and includes a shaft 210, a distal tip 220, a connector 240, an optical fiber 250, and a holding member 260. The shaft 210 is an elongated member extending along the axis O. The shaft 210 has a hollow and substantially cylindrical (tubular) shape with both end portions, a distal end portion 210d and a proximal end portion 210p being opened. An opening for exposing the distal end of the optical fiber 250 is formed on the outer peripheral surface on the distal end side of the shaft 210 (described later in FIG. 3). The optical fiber 250 and the holding member 260 are accommodated in (inside) the shaft 210. A void portion inside the shaft 210 excluding the optical fiber 250 and the holding member 260 is filled with a resin member 270. Note that the shaft 210 corresponds to the "hollow shaft".

The distal tip 220 is a member that is joined to the distal end portion 210d of the shaft 210 and advances ahead of other members in the lumen 110L of the catheter 1. As illustrated in FIG. 1, the distal tip 220 is an almost columnar member extending in the long axis direction of the light irradiation device 2. Here, it is preferable that an outer diameter $\Phi 3$ of the distal tip 220 and the shaft 210 (in other words, outer diameter $\Phi 3$ of the light irradiation device 2) is larger than the opening diameter $\Phi 1$ of the through-hole 120h of the catheter 1 and smaller than an inner diameter $\Phi 2$ of the shaft 110 and the light transmitting portion 139 of the catheter 1 ($\Phi 1 < \Phi 3 < \Phi 2$).

The connector 240 is a member arranged on the proximal end side of the light irradiation device 2 and gripped by the operator. The connector 240 includes a connection portion 241 having a substantially cylindrical shape and a pair of blades 242. A distal end portion of the connection portion 241 is joined to the proximal end portion 210p of the shaft 210, and a proximal end portion of the connection portion 241 is joined to the blades 242. The blades 242 may have a structure that is integrally formed with the connector 240.

Figure 2:
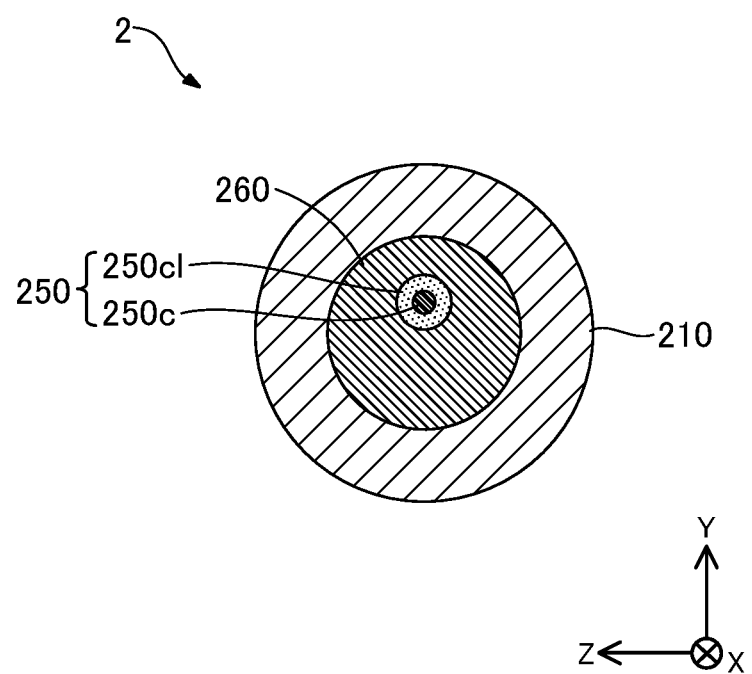
FIG. 2 is an explanatory diagram illustrating a cross-sectional configuration taken along line A-A of FIG. 1.

FIG. 2 is an explanatory diagram illustrating a cross-sectional configuration taken along line A-A in FIG. 1. The X-axis, Y-axis, and Z-axis illustrated in FIG. 2 correspond to the X-axis, Y-axis, and Z-axis respectively in FIG. 1. As illustrated in the figure, the optical fiber 250 includes a core 250c extending in the long axial direction (axis O direction) of the light irradiation device 2, and a clad 250cl that covers an outer peripheral surface (outer surface) of the core 250c. The core 250c is disposed substantially in the center of the clad 250cl and has a higher optical refractive index than of the clad 250cl. The clad 250cl has a uniform refractive index. The optical fiber 250 transmits the light by total light reflection using a difference in refractive index between the core 250c and the clad 250cl. In this optical fiber 250, the clad 250cl corresponds to a "covering layer" that covers the core 250c and corresponds to a "member constituting the outer surface of the optical fiber 250".

The optical fiber 250 according to the first embodiment is a plastic optical fiber in which the core 250c and the clad 250cl are both made of a resin. The core 250c can be made of e.g. a polymethylmetacrylate (PMMA), a polystyrene, a polycarbonate, a deuterated polymer, a fluorine-based polymer, a silicon-based polymer, a norbornene-based polymer, or the like. The core 250c is classified into a single-mode and a multi-mode depending on the number of modes for propagating the light, but either the single-mode or the multi-mode may be used in the first embodiment. Additionally, in the case of the multi-mode core 250c, the core 250c is classified into a step index and a graded index depending on a refractive index distribution, but either the step index or the graded index may be used in the first embodiment. The clad 250cl can be made of e.g. a fluorine-based polymer. For the optical fiber 250, a quartz glass optical fiber or a multi-component glass optical fiber may be employed instead of the plastic optical fiber. A longitudinal length of the optical fiber 250 can be arbitrarily determined.

As illustrated in FIG. 1, the distal end side of the optical fiber 250 is inserted inside the shaft 210 and fixed by the resin member 270. The proximal end side of the optical fiber 250 passes through the inside of the connector 240 and is pulled out to the outside. The proximal end portion of the optical fiber 250 is connected to a light source 3 via a connector not illustrated, directly, or indirectly via another optical fiber. The light source 3 is e.g. a laser light generator that generates a laser light at any wavelength.

Figure 3:
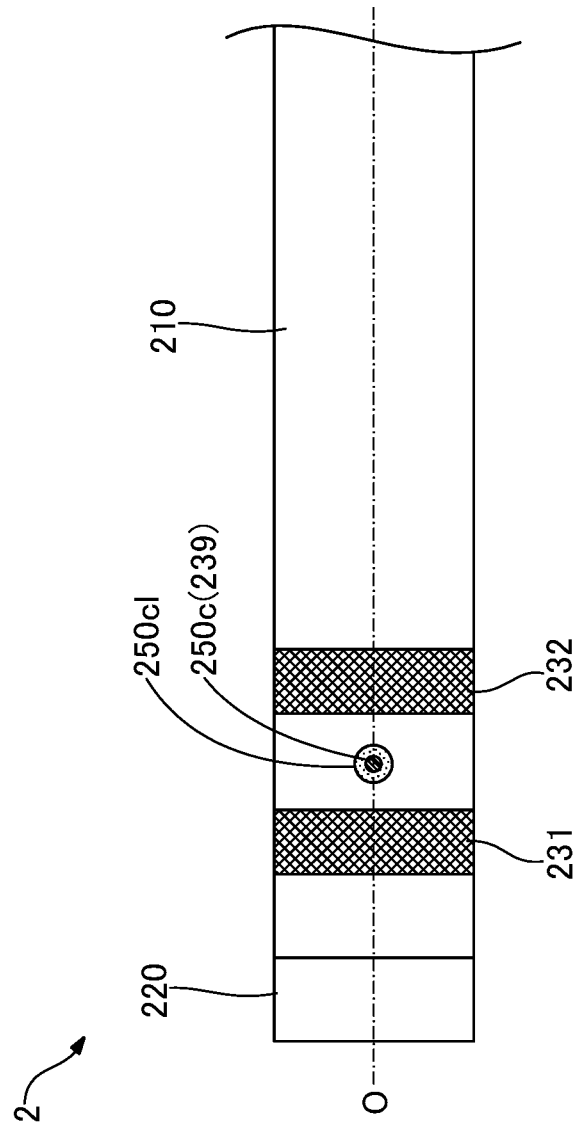
FIG. 3 is a top view of a light irradiation device viewed from direction B in FIG. 1.

FIG. 3 is a top view of the light irradiation device 2 viewed from direction B in FIG. 1. As illustrated in FIG. 1, a curved part 251 where the optical fiber 250 is curved in the +Y-axis direction is formed on the distal end portion of the optical fiber 250. As illustrated in FIG. 3, the distal end (distal end surface) of the optical fiber 250 is arranged so as to be exposed on the outer peripheral surface (outer surface) of the shaft 210. On the distal end of the optical fiber 250, the clad 250cl is removed and the core 250c is exposed. A laser light LT generated by the light source 3 and transmitted through the optical fiber 250 is emitted from the exposed core 250c. That means, the core 250c exposed on the distal end of the optical fiber 250 functionally serves as a light irradiation portion 239 that emits the light LT to the outside. Thus, in the configuration of the first embodiment, the distal end of the optical fiber 250 that emits the laser light LT is oriented in a direction intersecting with the long axial direction (axis O direction) of the light irradiation device 2, by the curved part 251 of the optical fiber 250. Thereby, the light LT is emitted from the core 250c (light irradiation portion 239) exposed on the distal end of the optical fiber 250 toward one direction of the side surface of the light irradiation device 2.

On the distal end (distal end surface) of the optical fiber 250, the core 250c may be subjected to a well-known process (e.g. a process of diagonally cutting a distal end surface, a process of forming a notch, a sandblast process, and a chemical process). A resin body or a light reflecting mirror for transmitting, refracting, or amplifying the laser light LT may be disposed on or near the distal end of the core 250c. The resin body can be formed, for example, by applying an acrylic ultraviolet-curable resin containing dispersed fine quartz powder, and curing the resin using ultraviolet light.

The holding member 260 is a member for retaining a shape (curved shape) of the curved part 251 of the optical fiber 250. The holding member 260 is disposed inside the shaft 210 and at a position of the curved part 251 of the optical fiber 250 (FIG. 1). The holding member 260 is arranged so as to cover the entire outer peripheral surface of the curved part 251 of the optical fiber 250 (FIG. 2). The holding member 260 is made of a light transmissive resin. Here, light transmissive resin means a resin that is transparent or translucent and has a property of transmitting light. As the light transmissive resin, for example, any resin such as an epoxy resin filled with an inorganic powder can be used. In the light transmissive resin used for the holding member 260, a light transmissivity in a wavelength range used in PDT or NIR-PIT (e.g. 650 nm to 700 nm) is preferably higher than the light transmissivity in another wavelength range. The holding member 260 may be formed by mixing plural different types of light transmissive resins.

This light transmitting holding member 260 has a refractive index 6R lower than a refractive index R5 of the member constituting the outer surface of the optical fiber 250 (i.e. clad 250cl) (R6<R5). In addition, the resin member 270 has a refractive index R7 lower than the refractive index R6 of the holding member 260 (R7<R6). That means, the relationship between the refractive index R5 of the clad 250cl, the refractive index R6 of the holding member 260, and the refractive index R7 of the resin member 270 is represented by "R7<R6<R5". Representative values such as catalogue values can be used for the refractive index R5 of the clad 250cl, the refractive index R6 of the holding member 260, and the refractive index R7 of the resin member 270.

Here, it is assumed that a first member and a second member having different refractive indices are arranged adjacent to each other. In this case, generally, the greater a difference in refractive index between the first member and the second member is, the more likely it is that a light advancing from the first member to the second member is totally reflected at a boundary surface between the first and second members (i.e. the light does not advance to the second member). On the other hand, the smaller the difference in refractive index between the first member and the second member, the more likely it is that the light advances from the first member to the second member while being refracted at the boundary surface between the first and second members. In this regard, in the light irradiation device 2 according to the first embodiment, the refractive index R6 of the holding member 260 is lower than the refractive index R5 of the clad 250cl constituting the outer surface of the optical fiber 250 (R6<R5). Thereby, for example, the light inside the optical fiber 250 can be reflected at a boundary between the clad 250cl and the holding member 260, compared to the case where the shape of the curved part 251 is retained using the holding member having a refractive index equivalent to or higher than the refractive index of the clad 250*cl*. Thus, the light leakage can be reduced via the holding member 260. In addition, the resin member 270 has a refractive index R7 lower than the refractive index R6 of the holding member 260 (R7<R6). For this reason, when comparing the resin member 270 with the holding member 260, the difference in refractive index between the resin member 270 and the clad 250*cl* is larger than the difference in refractive index between the holding member 260 and the clad 250*cl*. Consequently, the light leakage can be reduced via the resin member 270.

The optical fiber 250 consists only of the core 250*c* and need not have any covering layer such as the clad 250*cl*. In this case, the core 250*c* corresponds to the "member constituting the outer surface of the optical fiber 250". At this time, the refractive index R6 of the holding member 260 is lower than a refractive index R51 of the core 250*c* (R6<R51). The optical fiber 250 may further include a cover for covering the outer peripheral surface of the clad 250*cl*. In this case, the clad 250*cl* and the cover correspond to the "covering layer" for covering the core 250*c*, and the cover corresponds to the "member constituting the outer surface of the optical fiber 250". At this time, the refractive index R6 of the holding member 260 is lower than a refractive index R52 of the cover (R6<R52). Furthermore, when the cover is composed of a plurality of layers, the outermost cover corresponds to the "member constituting the outer surface of the optical fiber 250". At this time, the refractive index R6 of the holding member 260 is lower than a refractive index R53 of the outermost cover (R6<R53).

FIG. 1 will be explained again. Second marker portions 231 and 232 are further disposed on the shaft 210 of the light irradiation device 2. The second marker portions 231 and 232 function as marks indicating positions of the light irradiation portion 239 (i.e. the distal end of the optical fiber 250). As illustrated in FIG. 3, the second marker portion 231 is provided close to the distal end side of the light irradiation portion 239, and functions as a mark indicating a position of the distal end side of the light irradiation portion 239. The second marker portion 232 is provided close to the proximal end side of the light irradiation portion 239, and functions as a mark indicating a position of the proximal end side of the light irradiation portion 239. The second marker portions 231 and 232 are hollow members each having a substantially cylindrical shape. In the example of FIG. 1, the second marker portions 231 and 232 are respectively arranged in recess portions formed in the outer surface of the shaft 210 and are joined to the outer surface of the shaft 210. In other words, the second marker portions 231 and 232 are each embedded in the outer surface of the shaft 210 to surround the shaft 210 in a circumferential direction. It is noted that the second marker portions 231 and 232 may be joined to the outer surface of the shaft 210 without the recess portions, and may protrude from the outer surface of the shaft 210. At least one of the second marker portions 231 and 232 may be omitted.

The first marker portions 131 and 132 of the catheter 1 and the second marker portions 231 and 232 of the light irradiation device 2 can be formed of a radiopaque resin material or a radiopaque metal material. For example, when a resin material is used, the first marker portions 131 and 132 and the second marker portions 231 and 232 can be formed by using a mixture of a radiopaque material, such as bismuth trioxide, tungsten, or barium sulfate, and a resin material, such as a polyamide resin, a polyolefin resin, a polyester resin, a polyurethane resin, a silicon resin, or a fluororesin. When a metal material is used, for example, the first marker portions 131 and 132 and the second marker portions 231 and 232 can be formed of a radiopaque material such as gold, platinum, tungsten, or an alloy containing these elements (for example, a platinum-nickel alloy).

The shaft 110 of the catheter 1, the shaft 210 of the light irradiation device 2, and the resin member 270 of the light irradiation device 2 are preferably antithrombotic, flexible, and biocompatible, and can be formed of a resin material or a metal material. For example, a polyamide resin, a polyolefin resin, a polyester resin, a polyurethane resin, a silicon resin, a fluororesin, and the like can be employed as the resin material. For example, stainless steel such as SUS304, a nickel-titanium alloy, a cobalt-chromium alloy, tungsten steel and the like can be employed as the metal material. Further, the shaft 110 and the shaft 210 can be formed as a bonded structure in which a plurality of the above-mentioned materials are combined. The distal tip 120 of the catheter 1 and the distal tip 220 of the light irradiation device 2 are preferably flexible, and can be formed of, for example, a resin material such as polyurethane and a polyurethane elastomer. The connector 140 of the catheter 1 and the connector 240 of the light irradiation device 2 can be formed of a resin material such as a polyamide, a polypropylene, a polycarbonate, a polyacetal, and a polyether sulfone.

Figure 4:
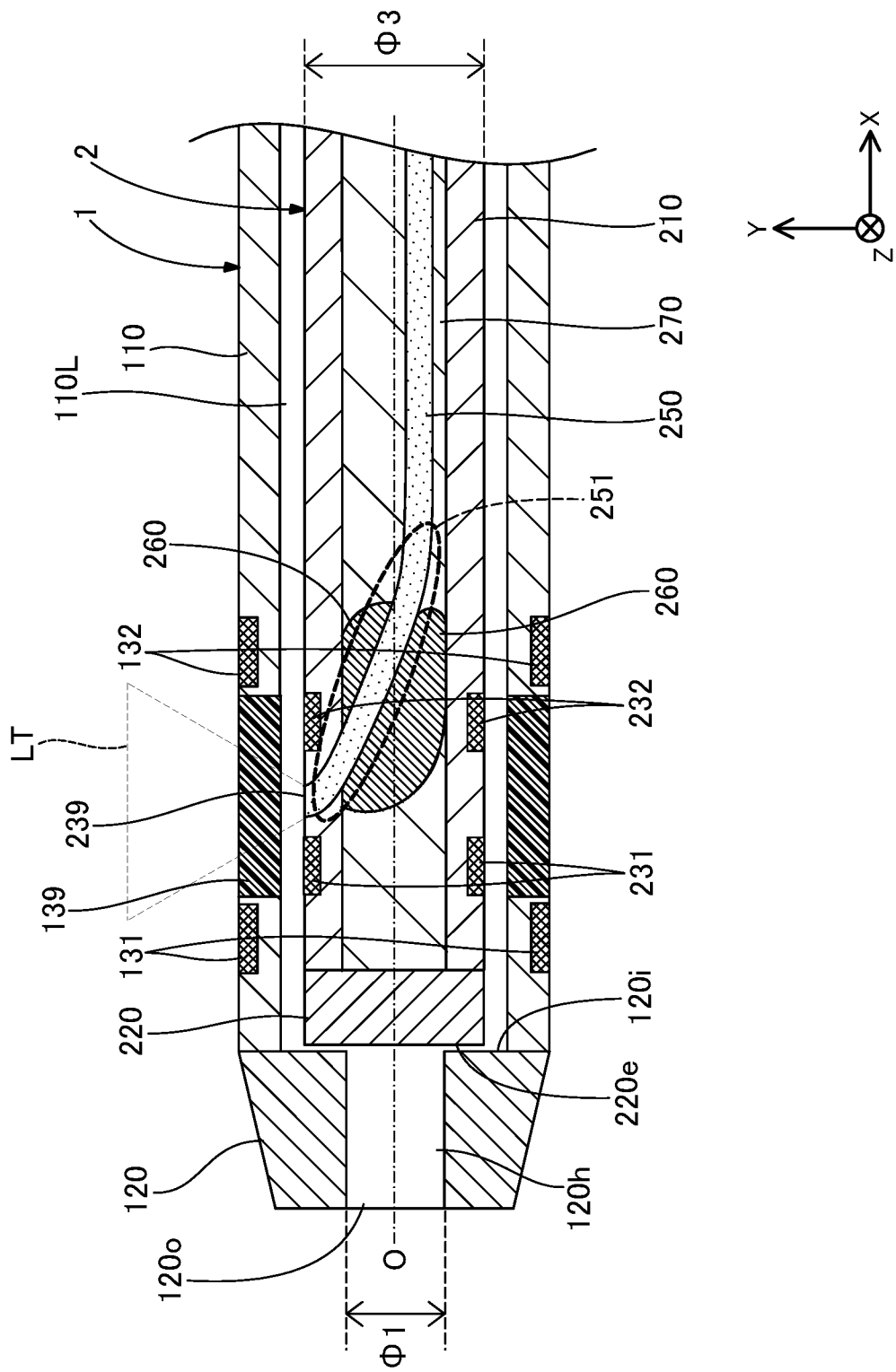
FIG. 4 is an explanatory diagram illustrating a usage state of the light irradiation system.

FIG. 4 is an explanatory diagram illustrating a usage state of the light irradiation system. A method of using the light irradiation system will be described with reference to FIGS. 1 and 4. First, an operator inserts a guide wire into a living body lumen. Next, the operator inserts a proximal end side of the guide wire from the opening 120*o* of the distal tip 120 of the catheter 1 illustrated in FIG. 1, through the lumen 110L so that the guide wire protrudes from the opening 140*o* of the connector 140. Subsequently, the operator pushes the catheter 1 into the living body lumen along the guide wire, and the light transmitting portion 139 of the catheter 1 is delivered to a target site for light irradiation (for example, in the case of NIR-PIT, a vicinity of a cancer cell). Thus, by inserting the guide wire from the through-hole 120*h* formed in the distal tip 120 of the catheter 1, the operator can easily deliver the catheter 1 to the target site in the living body lumen. It is noted that, during delivery, the operator can position the catheter 1 in the living body lumen, while observing, in an X-ray image, the positions of the first marker portions 131 and 132 arranged in the vicinity of the light transmitting portion 139. Afterwards, the surgeon removes the guide wire from the catheter 1.

Next, the operator inserts the light irradiation device 2 from the opening 140*o* of the connector 140 of the catheter 1. The operator pushes the light irradiation device 2 toward the distal end side of the catheter 1, along the lumen 110L of the catheter 1. Here, as described above, if the outer diameter Φ3 of the light irradiation device 2 is smaller than the diameter Φ2 of the lumen 110L of the catheter 1 and larger than the diameter Φ1 of the through-hole 120*h* of the distal tip 120, a distal end surface 220*e* of the light irradiation device 2 abuts against the inner surface 120*i* of the distal tip 120 when the light irradiation device 2 is inserted into the catheter 1, and thus, it is possible to prevent the light irradiation device 2 from being advanced beyond the distal end of the catheter 1 (FIG. 4).

After that, the operator aligns the light irradiation portion 239 (distal end of the optical fiber 250) with the light transmitting portion 139 in the direction of the axis O (X-axis direction), while observing, in an X-ray image, a positional relationship between the first marker portions 131 and 132 and the second marker portions 231 and 232. Thus, the laser light LT emitted from the light irradiation portion 239 (distal end of the optical fiber 250) can be transmitted through the light transmitting portion 139 of the catheter 1 and emitted to a living tissue on the outside. It is noted that, in the catheter 1 according to the first embodiment, the light transmitting portion 139 is provided in the entire circumferential direction. Therefore, in the light irradiation system according to the first embodiment, the operator only needs to achieve alignment between the light transmitting portion 139 and the light irradiation portion 239 in the direction of the axis O (X-axis direction), and does not need to achieve alignment between the light transmitting portion 139 and the light irradiation portion 239 in the circumferential direction.

As explained above, in the light irradiation device 2 according to the first embodiment, while the distal end of the optical fiber 250 is oriented in a direction intersecting with the long axial direction (axis O direction) of the light irradiation device 2 by the curved part 251, the shape of the curved part 251 is retained by the holding member 260 (FIG. 4). Thereby, for example, movement of the optical fiber by using a guide means simplifies the configuration of the light irradiation device 2 compared to a configuration in which the distal end of the optical fiber is oriented in a direction intersecting with the long axial direction of the light irradiation device, so that the diameter of the light irradiation device 2 can be decreased. In addition, the refractive index R6 of the holding member 260 is lower than the refractive index R5 of the clad 250*cl* (member constituting the outer surface of the optical fiber 250). Thereby, as explained in FIG. 2, for example, the light inside the optical fiber 250 can be reflected at the boundary between the clad 250*cl* and the holding member 260, compared to the case where the shape of the curved part 251 is retained using the holding member having a refractive index equivalent to or higher than the refractive index of the clad 250*cl*. As a result, the light irradiation device 2 according to the first embodiment makes it possible to reduce light leakage from the inside of the optical fiber 250.

In the light irradiation device 2 according to the first embodiment, the proximal end side with respect to the holding member 260 within the shaft 210 (hollow shaft) is filled with the resin member 270. Thereby, the elongated shape of the light irradiation device 2 can be easily retained. In addition, the refractive index R7 of the resin member 270 is lower than the refractive index R6 of the holding member 260. Consequently, as explained in FIG. 2, the light leakage can be reduced via the resin member 270.

Further, the light irradiation system according to the first embodiment separately includes the light irradiation device 2, and the catheter 1 having the light transmitting portion 139 for transmitting the inside light LT to the outside, which is disposed at a position corresponding to the distal end (i.e. the light irradiation portion 239) of the optical fiber 250. Consequently, the degree of freedom in designing the device can be improved and also the range of procedures can be expanded.

Second Embodiment

Figure 5:
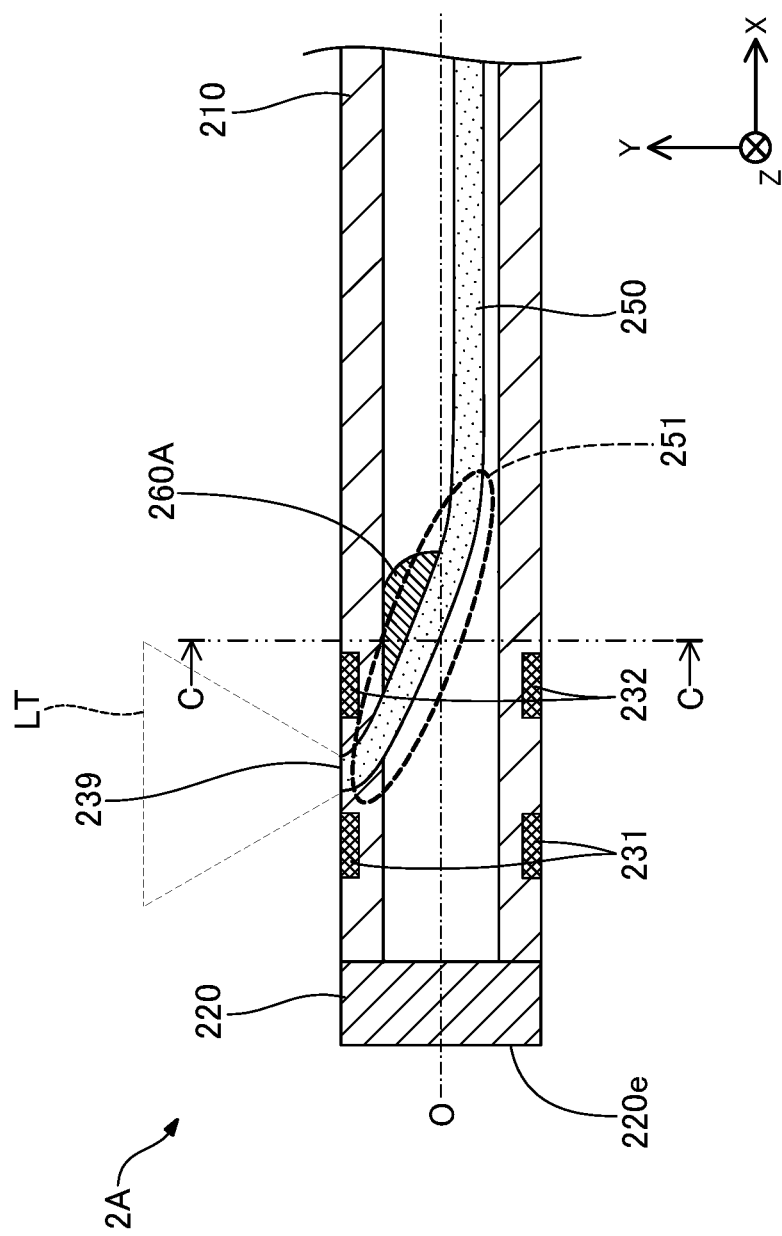
FIG. 5 is an explanatory diagram illustrating a configuration of a light irradiation device according to the second embodiment.
Figure 6:
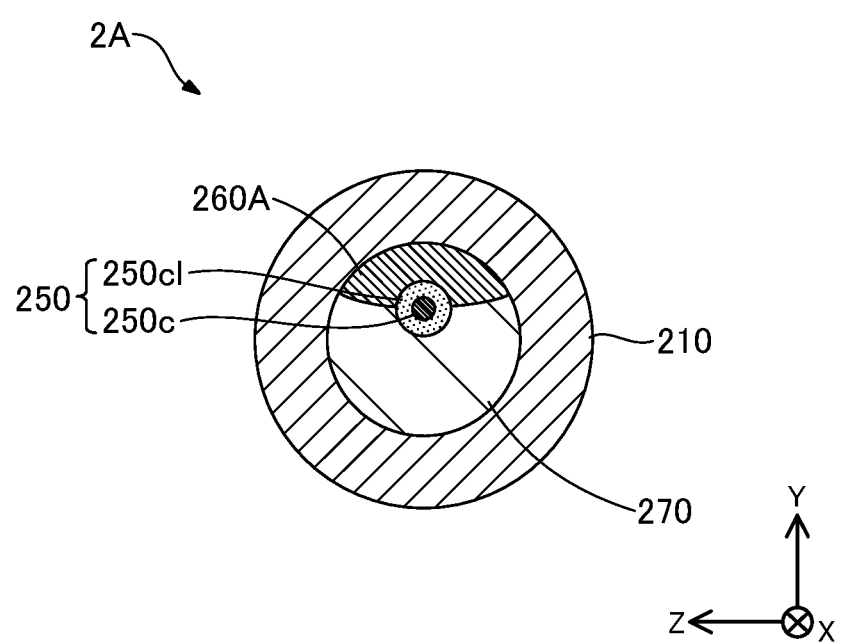
FIG. 6 is an explanatory diagram illustrating a cross-sectional configuration taken along line C-C of FIG. 5.

FIG. 5 is an explanatory diagram illustrating a configuration of a light irradiation device 2A according to the second embodiment. FIG. 6 is an explanatory diagram illustrating a cross-sectional configuration taken along line C-C of FIG. 5. A light irradiation system according to the second embodiment includes the catheter 1 explained in the first embodiment and the light irradiation device 2A illustrated in FIG. 5 and FIG. 6. The light irradiation device 2A includes a holding member 260A instead of the holding member 260 and does not include the resin member 270. The holding member 260A is arranged adjacent to the inner peripheral side of the curved part 251 of the optical fiber 250. The inner peripheral side of the curved part 251 means the inner side of the curved part on the outer peripheral surface of the optical fiber 250, and means, in the examples of FIG. 5 and FIG. 6, the +Y-axis direction side. The resin member 270 is disposed on the outer peripheral side (FIG. 5 and FIG. 6: −Y-axis direction side) of the curved part 251 of the optical fiber 250. A dimensional relationship in refractive index between the clad 250*cl*, the holding member 260A, and the resin member 270 is the same as in the first embodiment.

In this way, the configuration of the holding member 260A of the light irradiation device 2A can be modified in various ways, and the holding member 260A may be disposed only on the inner peripheral side of the curved part 251 of the optical fiber 250. In the example of FIG. 6, the holding member 260A is disposed on the inner peripheral side of the curved part 251 over a range of about 170 degrees in the circumferential direction, but the range in which the holding member 260A is arranged can be arbitrarily changed. The angular range may be e.g. 30 degrees, 90 degrees, or 270 degrees. In the examples of FIG. 5 and FIG. 6, although the outer peripheral side of the curved part 251 is filled with the resin member 270, the outer peripheral side of the curved part 251 need not be filled with the resin member 270, and may be e.g. a void.

Also, the light irradiation system according to the second embodiment as described above makes it possible to exhibit an effect similar to that in the first embodiment described above. In addition, in the light irradiation device 2A according to the second embodiment, the shape of the curved part 251 of the optical fiber 250 can be retained from at least the inner peripheral side of the curved part 251. The inner peripheral side of the curved part 251 is, in other words, a direction in which the distal end of the optical fiber 250 is oriented (i.e. a direction toward the light irradiation portion 239) and is the direction in which the light LT is emitted from the optical fiber 250. Herein, in general, the whole of the materials constituting the holding member 260A has a refractive index higher than of air. Thus, the light leakage in the direction not for the light emission from the optical fiber 250 can be further reduced, by leaving a void on the outer peripheral side (direction in which the light is not emitted from the optical fiber 250) of the curved part 251 without disposing the holding member 260A and the resin member 270, as in the light irradiation device 2A according to the second embodiment.

Third Embodiment

Figure 7:
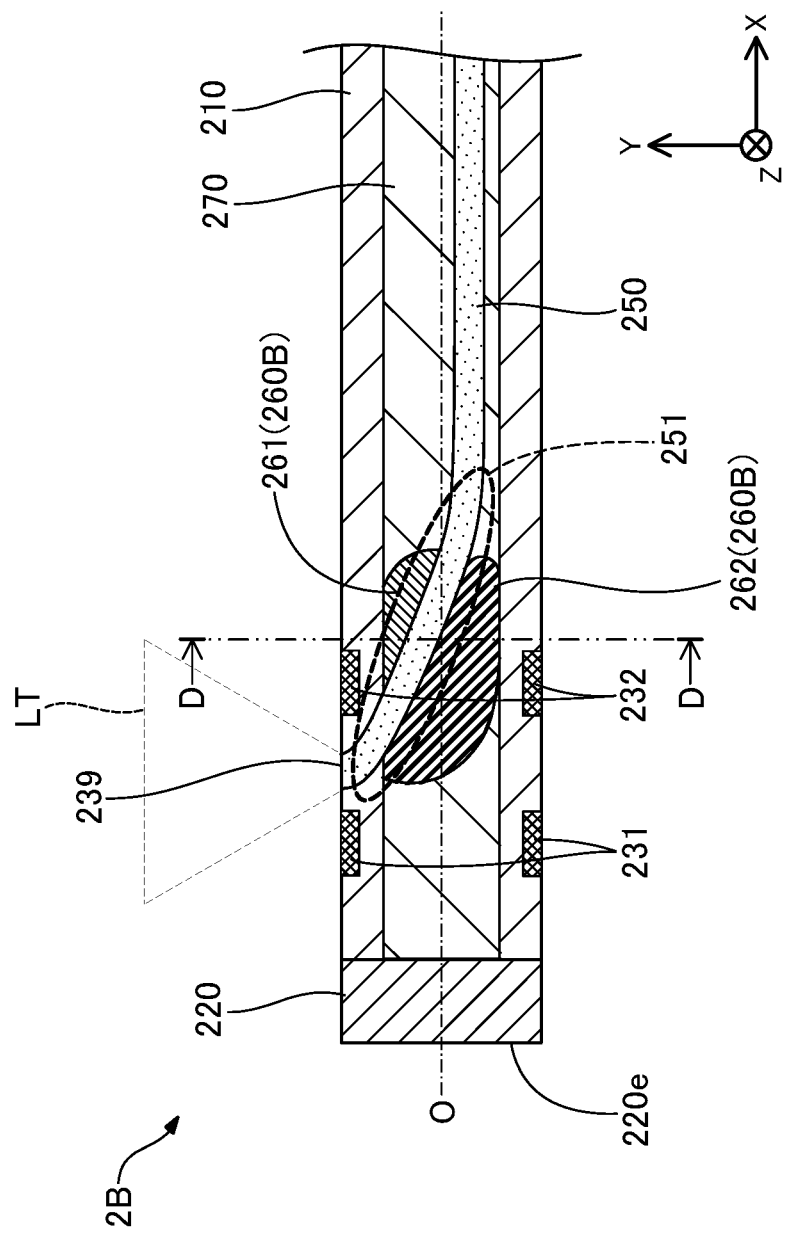
FIG. 7 is an explanatory diagram illustrating a configuration of a light irradiation device according to the third embodiment.
Figure 8:
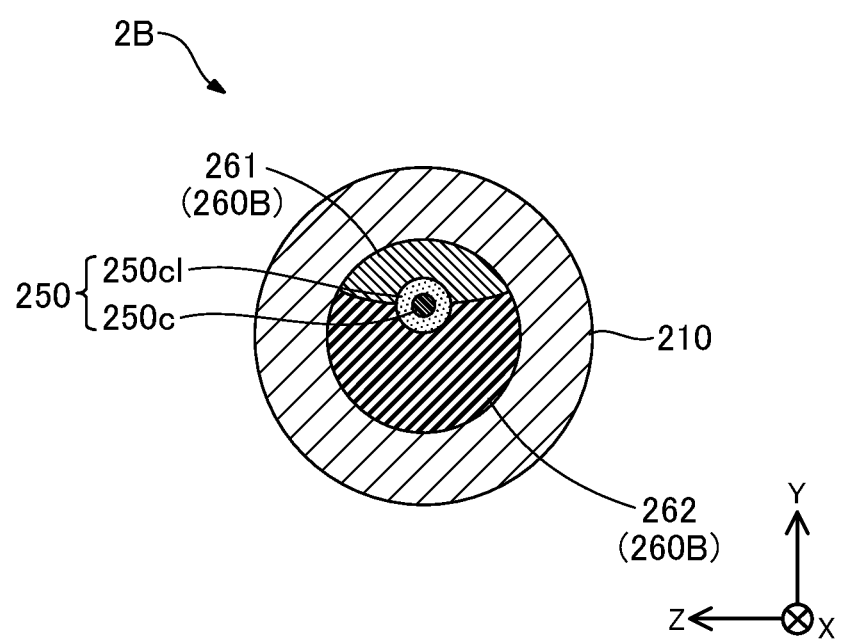
FIG. 8 is an explanatory diagram illustrating a cross-sectional configuration taken along line D-D of FIG. 7.

FIG. 7 is an explanatory diagram illustrating a configuration of a light irradiation device 2B according to the third embodiment. FIG. 8 is an explanatory diagram illustrating a cross-sectional configuration taken along line D-D of FIG. 7. A light irradiation system according to the third embodiment includes the catheter 1 explained in the first embodiment and the light irradiation device 2B illustrated in FIG. 7 and FIG. 8. The light irradiation device 2B includes a holding member 260B instead of the holding member 260. The holding member 260B includes an inner holding member 261 and an outer holding member 262.

The inner holding member 261 is arranged adjacent to the inner peripheral side of the curved part 251 of the optical fiber 250. The outer holding member 262 is arranged adjacent to the outer peripheral side of the curved part 251 of the optical fiber 250. In the example of FIG. 8, the inner holding member 261 is disposed on the inner peripheral side of the curved part 251 over a range of about 170 degrees in the circumferential direction, and the outer holding member 262 is disposed on the outer peripheral side of the curved part 251 over the remaining angular range (range of about 190 degrees) in the circumferential direction. However, the angular range in which the inner holding member 261 is disposed in the circumferential direction and the angular range in which the outer holding member 262 is disposed in the circumferential direction can be arbitrarily changed.

The inner holding member 261 and the outer holding member 262 are each made of different light transmissive resins. The outer holding member 262 has a refractive index $R62$ lower than a refractive index $R61$ of the inner holding member 261 ($R62<R61$). As in the first embodiment, the refractive indices $R61$ and $R62$ of the holding member 260B (inner holding member 261 and outer holding member 262) are both lower than the refractive index $R5$ of the clad $250cl$ constituting the outer surface of the optical fiber 250. Thus, a dimensional relationship therebetween is represented by $R62<R61<R5$.

As described above, the configuration of the holding member 260B of the light irradiation device 2B can be modified in various ways, and the holding member 260B may include the inner holding member 261 and the outer holding member 262 which are each made of different light transmissive resins. Also, the light irradiation system according to the third embodiment as described above makes it possible to exhibit an effect similar to that in the first embodiment described above. In the light irradiation device 2B according to the third embodiment, the shape (curved shape) of the curved part 251 can be firmly retained from different directions of the inner peripheral side and the outer peripheral side of the curved part 251. In addition, the refractive index $R62$ of the outer holding member 262 disposed on the outer peripheral side (the opposite side to the light LT-emitting side, i.e. −Y-axis direction in the example of FIG. 7) of the curved part 251 is lower than the refractive index $R61$ of the inner holding member 261 disposed on the inner peripheral side (the light LT-emitting side, i.e. +Y-axis direction in the example of FIG. 7) of the curved part 251. For this reason, when comparing the outer holding member 262 with the inner holding member 261, the difference in refractive index between the outer holding member 262 and the clad $250cl$ is larger than the difference in refractive index between the inner holding member 261 and the clad $250cl$. Thus, the light leakage from the outer holding member 262 arranged in the direction not for the light emission from the optical fiber 250 can be more reduced compared to the light leakage from the inner holding member 261 arranged in the direction of the light emission from the optical fiber 250.

In the light irradiation device 2B according to the third embodiment, the dimensional relationship between the refractive index $R61$ of the inner holding member 261 and the refractive index $R62$ of the outer holding member 262 may be reversed ($R61<R62$). Also, the refractive index $R61$ of the inner holding member 261 and the refractive index $R62$ of the outer holding member 262 may be substantially equal. Also in this way, the same effect as in the first embodiment can be exhibited, and the shape of the curved part 251 can be firmly retained from different directions of the inner peripheral side and the outer peripheral side of the curved part 251.

Fourth Embodiment

Figure 9:
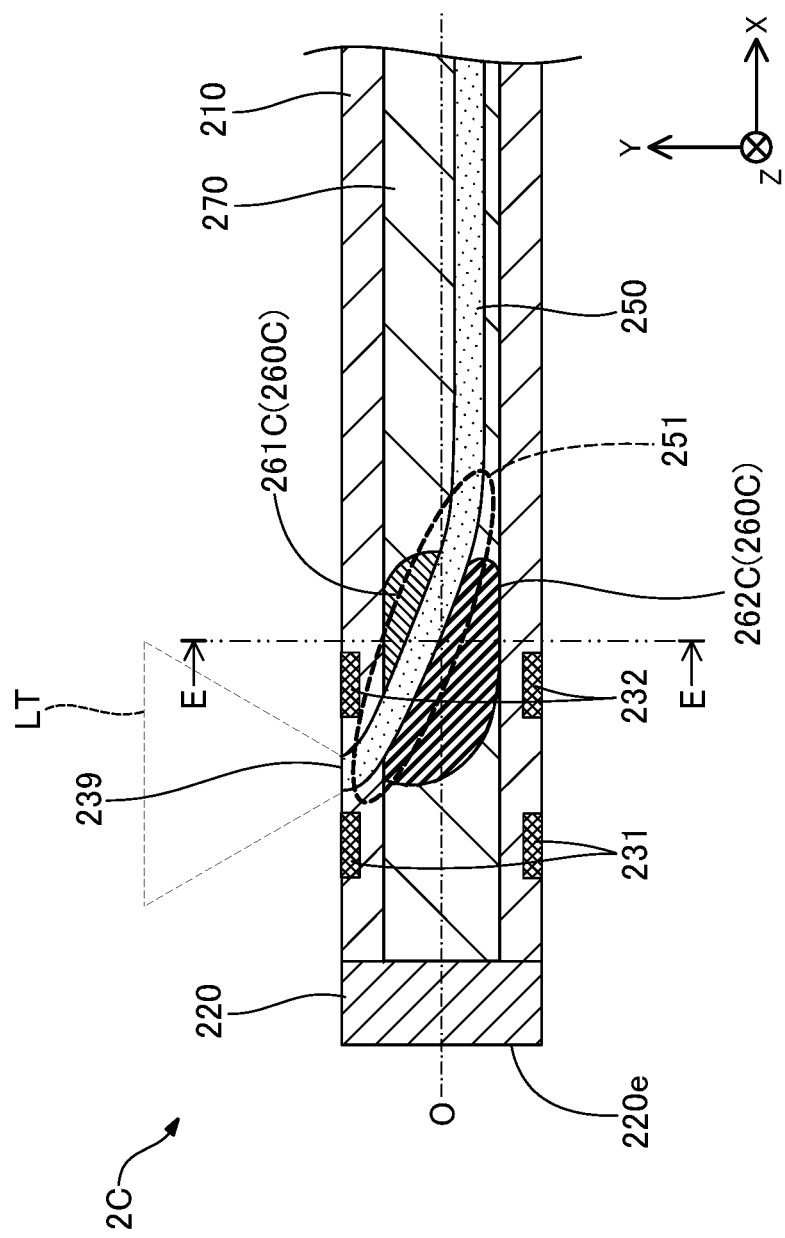
FIG. 9 is an explanatory diagram illustrating a configuration of a light irradiation device according to the fourth embodiment.
Figure 10:
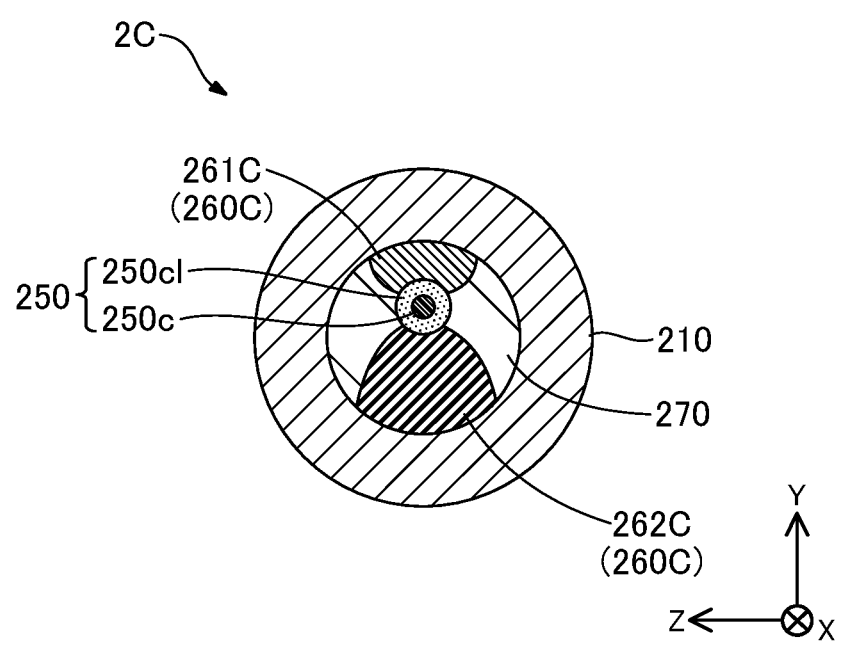
FIG. 10 is an explanatory diagram illustrating a cross-sectional configuration taken along line E-E of FIG. 9.

FIG. 9 is an explanatory diagram illustrating a configuration of a light irradiation device 2C according to the fourth embodiment. FIG. 10 is an explanatory diagram illustrating a cross-sectional configuration taken along line E-E of FIG. 9. A light irradiation system according to the fourth embodiment includes the catheter 1 explained in the first embodiment and the light irradiation device 2C illustrated in FIG. 9 and FIG. 10. The light irradiation device 2C includes a holding member 260C instead of the holding member 260. The holding member 260C includes an inner holding member 261C and an outer holding member 262C.

As illustrated in FIG. 10, the inner holding member 261C is disposed on the inner peripheral side of the curved part 251 of the optical fiber 250 over a range of about 100 degrees in the circumferential direction. Similarly, the outer holding member 262C is disposed on the outer peripheral side of the curved part 251 of the optical fiber 250 over a range of about 100 degrees in the circumferential direction. In the examples of FIG. 10, although a portion in the remaining angle range in the circumferential direction is filled with the resin member 270, the portion in the remaining angle range in the circumferential direction of the curved part 251 need not be filled with the resin member 270, and may be e.g. a void. The materials of the inner holding member 261C and the outer holding member 262C are the same as in the third embodiment. A dimensional relationship in refractive index between the inner holding member 261C, the outer holding member 262C, and the clad $250cl$ is the same as in the third embodiment ($R62<R61<R5$).

As described above, the configuration of the holding member 260C of the light irradiation device 2C can be modified in various ways, and the holding member 260C may include the inner holding member 261C and the outer holding member 262C, which are arranged apart from each other in the circumferential direction. Also, the light irradiation system according to the fourth embodiment as described above makes it possible to exhibit an effect similar to those in the first and third embodiments described above.

Fifth Embodiment

Figure 11:
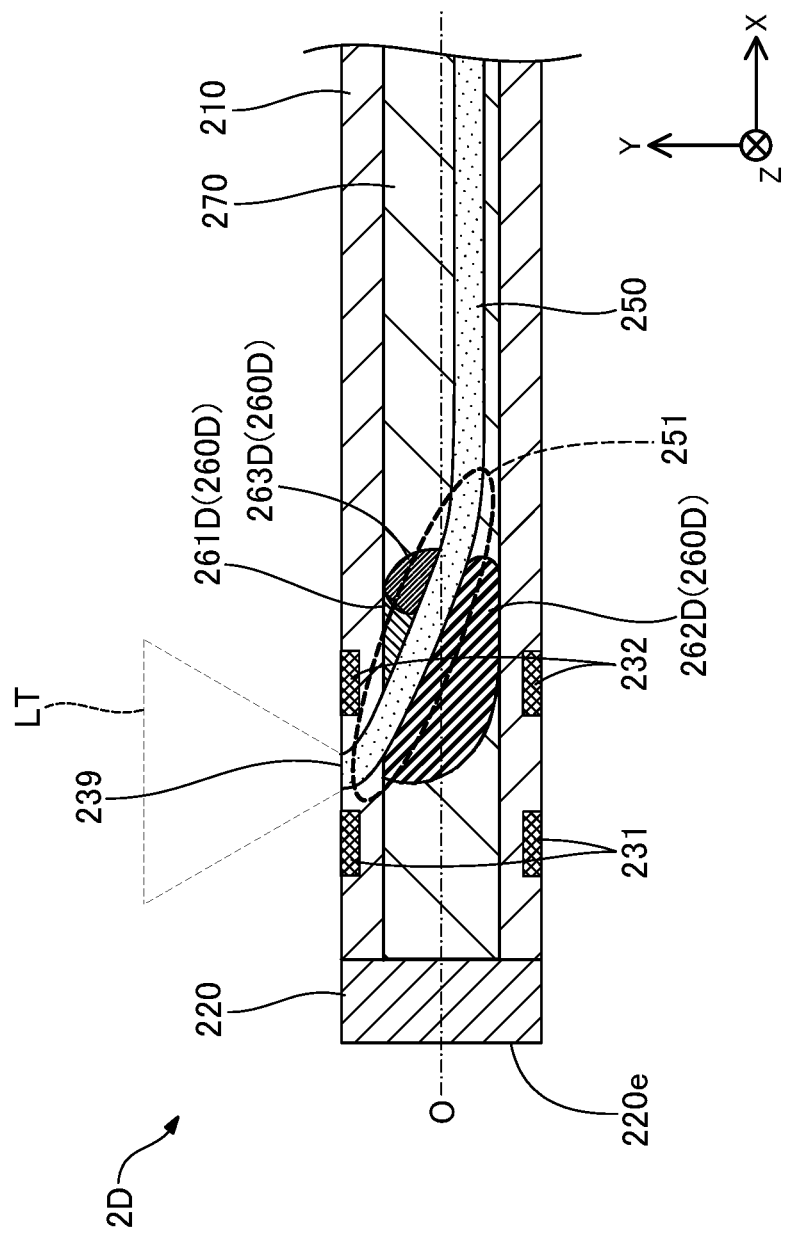
FIG. 11 is an explanatory diagram illustrating a configuration of a light irradiation device according to the fifth embodiment.

FIG. 11 is an explanatory diagram illustrating a configuration of a light irradiation device 2D according to the fifth embodiment. A light irradiation system according to the fifth embodiment includes the catheter 1 explained in the first embodiment and the light irradiation device 2D illustrated in FIG. 11. The light irradiation device 2D includes a holding member 260D instead of the holding member 260. The holding member 260D includes a first inner holding member 261D, a second inner holding member 263D, and an outer holding member 262D.

The first inner holding member 261D is disposed on the inner peripheral side of the curved part 251 of the optical fiber 250 and on the distal end side (−X-axis direction) of the light irradiation device 2D. The second inner holding member 263D is disposed on the inner peripheral side of the curved part 251 of the optical fiber 250 and on the proximal end side (+X-axis direction) of the light irradiation device 2D. The first inner holding member 261D and the second inner holding member 263D correspond to the "inner holding members". The outer holding member 262D is arranged adjacent to the outer peripheral side of the curved part 251 of the optical fiber 250. A peripheral range in which the first inner holding member 261D, the second inner holding member 263D, and the outer holding member 262D are disposed can be arbitrarily determined. For example, it is allowed to adopt a configuration in which the first inner holding member 261D and the second inner holding member 263D are disposed in a predetermined angular range in the circumferential direction, and the outer holding member 262D is disposed in the remaining angular range in the circumferential direction, as in the third embodiment. In addition, for example, it is allowed to adopt an arrangement in which the first inner holding member 261D and the second inner holding member 263D are disposed in a predetermined angular range in the circumferential direction, the outer holding member 262D is disposed in another predetermined angular range in the circumferential direction, and the remaining angular range in the circumferential direction is filled with the resin member 270, as in the fourth embodiment.

The first inner holding member 261D, the second inner holding member 263D, and the outer holding member 262D are each made of different light transmissive resins. The second inner holding member 263D has a refractive index R63 lower than the refractive index R61 of the first inner holding member 261D and higher than of the outer holding member 262D (R62<R63<R61). As in the first embodiment, the refractive indices R61, R63, and R62 of the holding member 260D (first inner holding member 261D, second inner holding member 263D, and outer holding member 262D) are all lower than the refractive index R5 of the clad 250cl constituting the outer surface of the optical fiber 250. Thus, a dimensional relationship therebetween is represented by R62<R63<R61<R5.

As described above, the configuration of the holding member 260D of the light irradiation device 2D can be modified in various ways, and the inner holding member of the holding member 260D may include the first inner holding member 261D and the second inner holding member 263D which are each made of different light transmissive resins. Three or more inner holding members may be disposed on the inner peripheral side of the curved part 251 of the optical fiber 250. Also, the light irradiation system according to the fifth embodiment as described above makes it possible to exhibit an effect similar to that in the first embodiment described above. In the light irradiation device 2D according to the fifth embodiment, since the inner holding member includes the first inner holding member 261D disposed on the distal end side and the second inner holding member 263D disposed on the proximal end side, a degree of the light leakage can be changed by controlling the refractive indices R61 and R63 of the first and second inner holding members 261D and 263D. The refractive index R63 of the second inner holding member 263D is lower than the refractive index R61 of the first inner holding member 261D and higher than the refractive index R62 of the outer holding member 262D. Thus, the light leakage from the outer holding member 262D arranged in the direction not for the light emission from the optical fiber 250 can be more reduced compared to the light leakage from the first and second inner holding members 261D and 263D arranged in the direction of the light emission from the optical fiber 250. Furthermore, the light leakage from the second inner holding member 263D disposed on the proximal end side can be more reduced compared to the light leakage from the first inner holding member 261D disposed on the distal end side.

Sixth Embodiment

Figure 12:
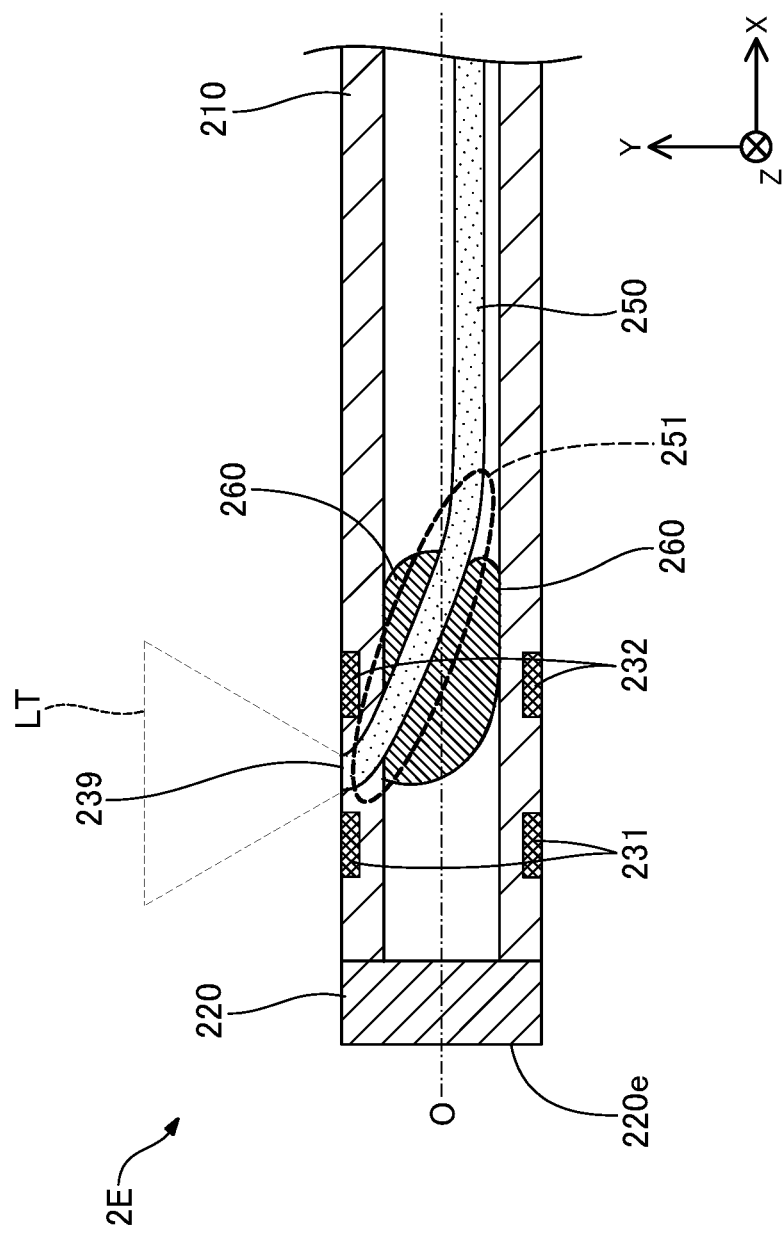
FIG. 12 is an explanatory diagram illustrating a configuration of a light irradiation device according to the sixth embodiment.

FIG. 12 is an explanatory diagram illustrating a configuration of a light irradiation device 2E according to the sixth embodiment. A light irradiation system according to the sixth embodiment includes the catheter 1 explained in the first embodiment and the light irradiation device 2E illustrated in FIG. 12. The light irradiation device 2E does not include the resin member 270 explained in the first embodiment, and a portion inside the shaft 210, where the optical fiber 250 and the holding member 260 are not accommodated, is a void. As described above, the configuration of the light irradiation device 2E can be modified in various ways, and the light irradiation device 2E need not include the resin member 270, and may include another reinforcing member in place of the resin member 270. As another reinforcing member, for example, a braided body or a coil body can be employed. Such a reinforcing member may be disposed inside the shaft 210 or embedded in a thick-walled portion of the shaft 210. Also, the light irradiation system according to the sixth embodiment as described above makes it possible to exhibit an effect similar to that in the first embodiment described above.

Seventh Embodiment

Figure 13:
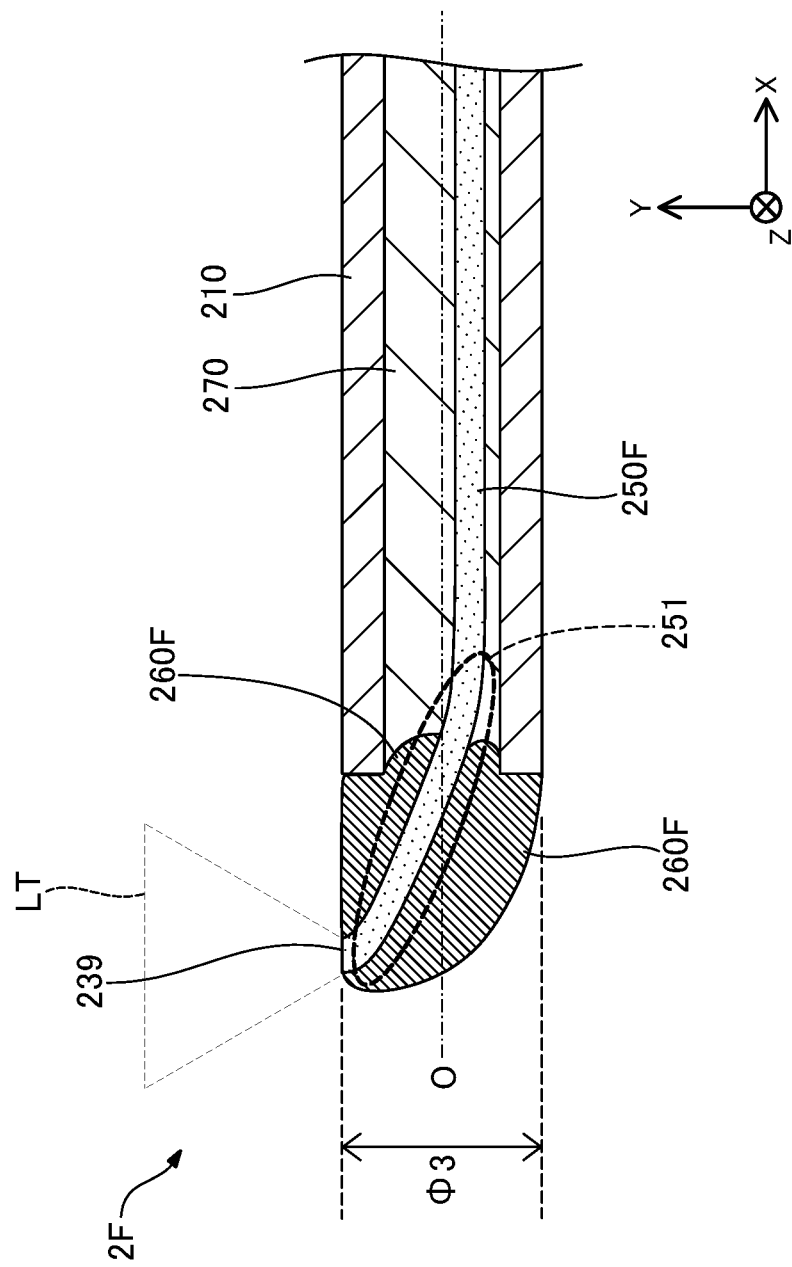
FIG. 13 is an explanatory diagram illustrating a configuration of a light irradiation device according to the seventh embodiment.

FIG. 13 is an explanatory diagram illustrating a configuration of a light irradiation device 2F according to a seventh embodiment. A light irradiation system according to the seventh embodiment includes the catheter 1 explained in the first embodiment and the light irradiation device 2F illustrated in FIG. 13. The light irradiation device 2F does not have the distal tip 220, and includes an optical fiber 250F instead of an optical fiber 250, and includes an optical fiber 250F instead of the optical fiber 250, and a holding member 260F instead of the holding member 260.

The optical fiber 250F is arranged such that a part of the distal end side of the curved part 251 protrudes from the distal end of the shaft 210. The protruding length of the curved part 251 can be arbitrarily determined. The holding member 260F covers the periphery of the curved part 251 protruding from the shaft 210. In other words, the holding member 260F covers the entire surface in the circumferential direction of the curved part 251 protruding from the shaft 210. The holding member 260F is shaped such that the diameter gradually decreases from the proximal end side toward the distal end side and the distal end portion is rounded. Since the holding member 260F is arranged along the curved part 251 that is curved in the +Y-axis direction, the shape of the holding member 260 with the decreasing diameter is asymmetric with respect to the axis O in the cross section illustrated in FIG. 13. The largest outer diameter of the holding member 260F is equal to the outer diameter Φ3 of the shaft 210 (in other words, the outer diameter Φ3 of the light irradiation device 2F. A material and a refractive index of the holding member 260F are the same as those in the first embodiment.

As described above, the configuration of the light irradiation device 2F can be modified in various ways, and the light irradiation device 2F may be configured such that the curved part 251 of the optical fiber 250F protrudes from the shaft 210, and the holding member 260F that covers the periphery of the protruding curved part 251 is further provided. At this time, the shape of the holding member 260F can be arbitrarily changed. For example, the holding member 260F need not cover the entire periphery of the curved part 251 protruding from the shaft 210, and may cover at least a part of the curved part 251. Also, the light irradiation system according to the seventh embodiment as described above makes it possible to exhibit an effect similar to that in the first embodiment described above. In the light irradiation device 2F according to the seventh embodiment, a part on the distal end side of the curved part 251, i.e. the distal end of the optical fiber 250F is protruded from the distal end of the shaft 210 (hollow shaft), so that the light LT emitted from the distal end of the optical fiber 250F can be prevented from being blocked by the shaft 210. In addition, since the holding member 260F covers the periphery of the protruding curved part 251, the periphery of the protruding curved part 251 can be protected.

Eighth Embodiment

Figure 14:
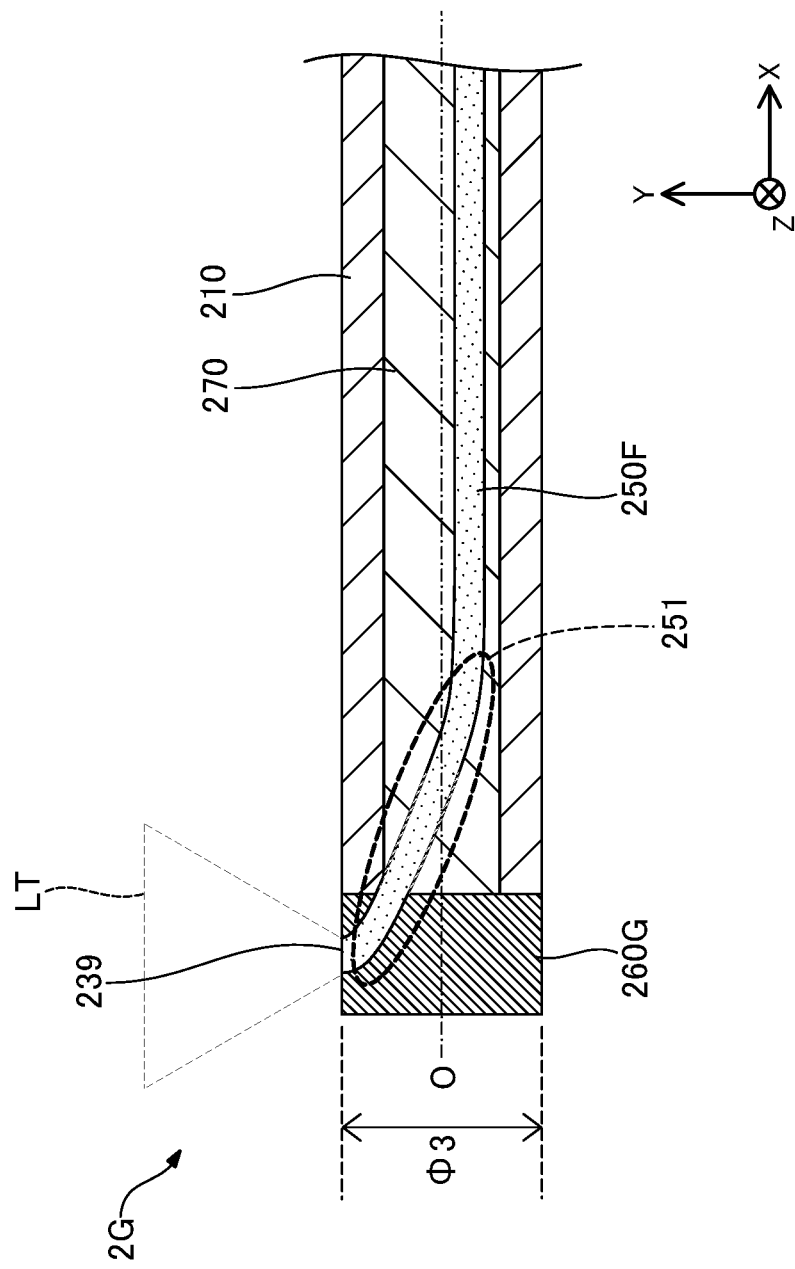
FIG. 14 is an explanatory diagram illustrating a configuration of a light irradiation device according to the eighth embodiment.

FIG. 14 is an explanatory diagram illustrating a configuration of a light irradiation device 2G according to the eighth embodiment. Alight irradiation system according to the eighth embodiment includes the catheter 1 explained in the first embodiment and the light irradiation device 2G illustrated in FIG. 14. The light irradiation device 2G has a holding member 260G having a shape different from that in the seventh embodiment, in the configuration in which the curved part 251 of the optical fiber 250F explained in the seventh embodiment protrudes from the shaft 210. The holding member 260G covers the periphery (entire surface in the circumferential direction) of the curved part 251 protruding from the shaft 210. The holding member 260G is an almost columnar member having a substantially constant outer diameter, and the outer diameter of the holding member 260G is substantially the same as the outer diameter Φ3 of the shaft 210. The holding member 260G is joined to the distal end portion of the shaft 210. For the joining, any joining agent such as an epoxy adhesive can be used. As described above, the configuration of the light irradiation device 2G can be modified in various ways, and may include the holding member 260G having a different shape from that in the seventh embodiment. Also, the light irradiation system according to the eighth embodiment as described above makes it possible to exhibit an effect similar to those in the first and seventh embodiments described above.

Ninth Embodiment

Figure 15:
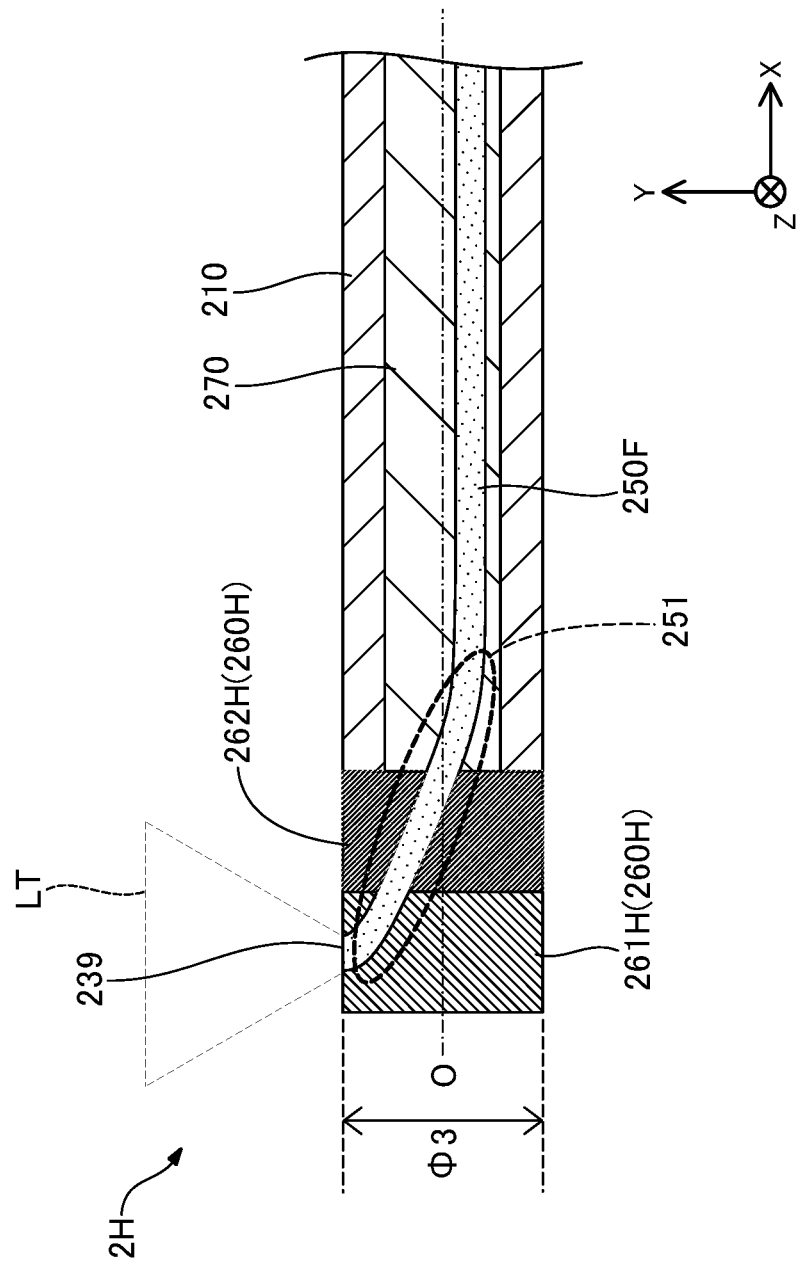
FIG. 15 is an explanatory diagram illustrating a configuration of a light irradiation device according to the ninth embodiment.

FIG. 15 is an explanatory diagram illustrating a configuration of a light irradiation device 2H according to the ninth embodiment. A light irradiation system according to the ninth embodiment includes the catheter 1 explained in the first embodiment and the light irradiation device 2H illustrated in FIG. 15. The light irradiation device 2H has a holding member 260H having a shape different from that in the seventh embodiment, in the configuration in which the curved part 251 of the optical fiber 250F explained in the seventh embodiment protrudes from the shaft 210. The holding member 260H includes a distal end side holding member 261H and a proximal end side holding member 262H. The distal end side holding member 261H is disposed on the distal end of the light irradiation device 2H to cover the distal periphery (entire surface in the circumferential direction) of the curved part 251 protruding from the shaft 210. The proximal end side holding member 262H is disposed between the distal end side holding member 261H and the shaft 210 to cover the proximal periphery (entire surface in the circumferential direction) of the curved part 251 protruding from the shaft 210. The distal end side holding member 261H and the proximal end side holding member 262H are both an almost columnar member having a substantially constant outer diameter. The outer diameter of the distal end side holding member 261H and the outer diameter of the proximal end side holding member 262H are both substantially equal to the outer diameter Φ3 of the shaft 210. As described above, the configuration of the light irradiation device 2H can be modified in various ways, and may include the holding member 260H having a different shape from that in the seventh embodiment. Also, the light irradiation system according to the ninth embodiment as described above makes it possible to exhibit an effect similar to those in the first and seventh embodiments described above.

Tenth Embodiment

FIG. 16 is an explanatory diagram illustrating a configuration of a light irradiation device 2I according to the tenth embodiment. A light irradiation system according to the tenth embodiment includes the catheter 1 explained in the first embodiment and the light irradiation device 2I illustrated in FIG. 16. The light irradiation device 2I has a shaft 210I instead of the shaft 210, an optical fiber 250I instead of the optical fiber 250, and a light irradiation portion 239I instead of the light irradiation portion 239.

Similarly to the shaft 210 according to the first embodiment, the shaft 210I has a hollow and almost cylindrical shape in which both a distal end portion and a proximal end portion are opened. Unlike the shaft 210 according to the first embodiment, the shaft 210I has no opening for exposing the distal end of the optical fiber 250I. A portion of the shaft 210I, on which the distal end of the optical fiber 250I abuts, is made of a light transmissive resin, and configured to allow transmission of the laser light LT. Similarly to the optical fiber 250 according to the first embodiment, the optical fiber 250I has the curved part 251 where the optical fiber 250I is curved in the +Y-axis direction, on the distal end portion. Unlike the optical fiber 250 according to the first embodiment, the optical fiber 250I is arranged such that its distal end (distal end surface) abuts on the inner peripheral surface of the shaft 210I. The light LT emitted from the core 250c exposed on the distal end of the optical fiber 250I is transmitted through the shaft 210I and emitted to the outside. Thereby, in the tenth embodiment, a part of the shaft 210I functionally serves as the light irradiation portion 239I.

As described above, the configuration of the light irradiation device 2I can be modified in various ways, and the distal end of the optical fiber 250I need not be disposed so as to be exposed on the outer peripheral surface of the shaft 210I. In this case, a portion of the shaft 210I, on which the distal end of the optical fiber 250I abuts, may have a thickness smaller than of the other portion to allow transmission of the light LT. In addition, a resin body or a light reflecting mirror for transmission, refraction, and amplification of the light LT may be disposed on the portion of the shaft 210I, on which the distal end of the optical fiber 250I abuts. The whole of the shaft 210I may be formed of the light transmissive resin. Also, the light irradiation system according to the tenth embodiment as described above makes it possible to exhibit an effect similar to that in the first embodiment described above.

Eleventh Embodiment

FIG. 17 is an explanatory diagram illustrating a configuration of a light irradiation system according to the eleventh embodiment. The light irradiation system according to the eleventh embodiment includes the catheter 1 explained in the first embodiment and a light irradiation device 2J illustrated in FIG. 17. The light irradiation device 2J does not have the shaft 210, the distal tip 220, and the connector 240 explained in the first embodiment, and is composed of an optical fiber 250J and a holding member 260J. A configuration of the optical fiber 250J is the same as of the optical fiber 250 explained in the first embodiment, and a configuration of the holding member 260J is the same as of the holding member 260 explained in the first embodiment. In this way, the configuration of the light irradiation device 2J can be modified in various ways, and need not include at least a part of each of the shaft 210, the distal tip 220, and the connector 240. Also, the light irradiation system according to the eleventh embodiment as described above makes it possible to exhibit an effect similar to that in the first embodiment described above. In addition, in the light irradiation device 2J according to the eleventh embodiment, the configuration of the light irradiation device 2J can be simplified, so that the light irradiation device 2J can be easily manufactured and a manufacturing cost of the light irradiation device 2J can be reduced. In addition, when the diameter of the light irradiation device 2J can be decreased, device delivery from a forceps port of a small diameter endoscope such as an oral endoscope or a nasal endoscope becomes possible.

Modifications of Embodiment

The disclosed embodiments are not limited to the above-described embodiments, and may be implemented in various modes without departing from the spirit of the disclosed embodiments. The following modifications can be applied, for example.

[First Modification]

In the first to eleventh embodiments above, examples of the configurations of the catheter 1, and the light irradiation devices 2, and 2A to 2J have been described. However, the configurations of the catheter 1 and the light irradiation device 2 can be modified in various ways. For example, the light irradiation system may be constituted by only the light irradiation device 2 without the catheter 1.

For example, a reinforcing layer formed of a braided body or a coil body may be embedded in the shaft 110 of the catheter 1 and the shaft 210 of the light irradiation device 2. Thus, it is possible to improve the torquability and the shape retention of the catheter 1 and the light irradiation device 2. For example, a coating formed of a hydrophilic or hydrophobic resin may be applied to the outer surface of the catheter 1 and the outer surface of the light irradiation device 2. Thus, the slidability of the catheter 1 in the living body lumen can be improved. Further, the slidability of the light irradiation device 2 in the lumen 110L of the catheter 1 can be improved. Moreover, the outer surface of the catheter 1 or the outer surface of the light irradiation device 2 may be coated with an antithrombotic material such as heparin. This makes it possible to suppress a decrease in laser output due to thrombus adhesion to the inner and outer surfaces of the catheter 1 and the outer surface of the light irradiation device 2 caused by the irradiation with the emission light (laser light) LT.

For example, the catheter 1 may include an expansion portion expandable in a radial direction (YZ-direction). For example, a balloon formed of a flexible thin film or a mesh body having wires arranged in a mesh shape can be used as the expansion portion. The expansion portion may be provided on at least one of the distal end side of the light transmitting portion 139 and the proximal end side of the light transmitting portion 139 in the shaft 110. Thus, after the catheter 1 is positioned in the living body lumen, the catheter 1 can be fixed in the living body lumen by expanding the expansion portion. Further, if a balloon is used as the expansion portion, the bloodstream at the site being irradiated with light can be blocked, and thus, it is possible to prevent that the bloodstream blocks the light.

For example, the catheter 1 may be configured as a multi-lumen catheter including a plurality of lumens different from the lumen 110L. Similarly, the light irradiation device 2 may be configured as a multi-lumen catheter including a separate lumen different from the lumen into which the first optical fiber 250 is inserted. In this case, the shaft 210 can be made using a hollow member having a substantially cylindrical shape, and the distal tip 220 can be provided with a through-hole extending along the direction of the axis O.

For example, the inner surface of the distal tip 120 of the catheter 1 and the outer surface of the distal tip 220 of the light irradiation device 2 may be formed of a magnetic material and may be configured to attract each other. Thus, as illustrated in FIG. 4, a state where the light irradiation device 2 is inserted into the catheter 1 and the distal tip 220 is pressed against the distal tip 120 can be easily maintained. For example, it is allowed to adopt a configuration in which the distal tip 120 of the catheter 1 is omitted and the distal end side of the shaft 110 is opened.

[Second Modification]

In the above first to eleventh embodiments, regarding the light irradiation devices 2, and 2A to 2J, examples of the configurations of the optical fibers 250, 250F, 250I, and 250J, and the holding members 260, 260A to 260H, and 260J have been described. However, these configurations can be modified in various ways. For example, the shape of the curved part 251 for allowing the distal end of the optical fiber 250 to intersect with the long axial direction of the light irradiation device 2 is not limited to the shape illustrated in the figures, and any shape can be adopted. For example, the optical fiber 250 may have a separate curved part different from the curved part 251 for allowing the distal end of the optical fiber 250 to intersect with the long axial direction of the light irradiation device 2. This curved part can be disposed e.g. on the proximal end side of the curved part 251. The shape of the curved part can be arbitrarily determined and may be e.g. a spiral shape, a wave shape, or a bellows shape, along the inner peripheral surface of the shaft 210.

For example, longitudinal ranges (axis O direction) of the holding member 260 arranged adjacent to the periphery of the curved part 251, the inner holding member arranged adjacent to the inner peripheral side of the curved part 251, and the outer holding member arranged adjacent to the outer peripheral side of the curved part 251 can be arbitrarily determined. For example, the outer holding member arranged adjacent to the outer peripheral side of the curved part 251 may be disposed up to the distal end (boundary surface between the shaft 210 and the distal tip 220) of the shaft 210.

For example, the light irradiation device 2 may include only the outer holding member arranged adjacent to the outer peripheral side of the curved part 251 without including the inner holding member arranged adjacent to the inner peripheral side of the curved part 251. For example, as in the fifth embodiment, the outer holding member arranged adjacent to the outer peripheral side of the curved part 251 may include a first outer holding member disposed on the distal end side and a second outer holding member disposed on the proximal end side. The outer holding member arranged adjacent to the outer peripheral side of the curved part 251 may include three or more outer holding members.

[Third Modification]

In the first to eleventh embodiments described above, the examples of the configurations of the light transmitting portion 139, and the light irradiation portions 239 and 239I have been described. However, the configurations of the light transmitting portion 139 and the light irradiation portion 239 can be modified in various ways. For example, the light transmitting portion 139 may be formed of a radiopaque material, to integrally form the light transmitting portion 139 and the first marker portions 131 and 132. Similarly, at least the distal end portion (light irradiation portion 239) of the clad 250*cl* may be formed of a radiopaque material to integrally form the light irradiation portion 239 and the second marker portions 231 and 232.

For example, the light transmitting portion 139 may be formed by thinning a part of the shaft 110. For example, at least one side of the light transmitting portion 139 may be formed as a notch (through hole that communicates between the inside and outside of the shaft) formed on the shaft 110. In this way, the light transmitting portion 139 can be easily formed. For example, the range in the axis O direction (X-axis direction) and the range in the circumferential direction (YZ-axis direction), where the light transmitting portion 139 is disposed, can be arbitrarily changed. Specifically, for example, the light transmitting portion 139 may be disposed over a wide range in the axis O direction.

For example, the catheter 1 may further include a separate marker portion disposed at any position, such as the distal end side and the proximal end side of the light transmitting portion 139. For example, the light irradiation device 2 may further include a separate marker portion disposed at any position, such as the distal end side and the proximal end side of the light transmitting portion 239. The shapes of the marker portions of the catheter 1 and the light irradiation device 2 can be arbitrarily determined, and may be a shape extending over the whole or a part of the circumferential direction (YZ direction), a shape extending in the axis O direction (X-axis direction), or a shape surrounding the periphery of the shaft. In addition, the distal tip 120 of the catheter 1 or the distal tip 220 of the light irradiation device 2 may be configured as the marker portions.

[Fourth Modification]

The configurations of the catheter 1, and the light irradiation devices 2, and 2A to 2J according to the first to eleventh embodiments, and the configurations of the catheter 1, and the light irradiation devices 2, and 2A to 2J according to the first to third modifications may be combined as appropriate. For example, the configuration explained in the sixth embodiment (configuration not including the resin member 270) may include the holding member 260 explained in the second to fifth embodiments or the seventh to ninth embodiments. For example, the configuration explained in the tenth embodiment (configuration in which the distal end of the optical fiber 250 abuts on the inner peripheral surface of the shaft 210) may include the holding member 260 explained in the second to fifth embodiments or the seventh to ninth embodiments. For example, the configuration explained in the eleventh embodiment (configuration not including the shaft 210, the distal tip 220, and the connector 240) may include the holding member 260 explained in the second to fifth embodiments or the seventh to ninth embodiments.

Although the aspects have been described based on the embodiments and the modifications, the embodiments of the above-described aspects are for facilitating understanding of the aspects, and do not limit the aspects. The aspects can be modified and improved without departing from the spirit of the aspects and the scope of the claims, and equivalent aspects are included in the aspects. Further, unless a technical feature is described as essential in the present specification, the technical feature may be omitted as appropriate.

DESCRIPTION OF REFERENCE NUMERALS

1 . . . Catheter
2, 2A to 2J . . . Light irradiation device
3 . . . Light source
110 . . . Shaft
120 . . . Distal tip
131, 132 . . . First marker portion
139 . . . Light transmitting portion
140 . . . Connector
141 . . . Connection portion
142 . . . Blade
210, 210I . . . Shaft
220 . . . Distal tip
231, 232 . . . Second marker portion
239, 239I . . . Light irradiation portion
240 . . . Connector
241 . . . Connection portion
242 . . . Blade
250, 250F, 250I, 250J . . . Optical Fiber
250*c* . . . Core
250*cl* . . . Clad
251 . . . Curved part
260, 260A to 260H, 260J . . . Holding member
261, 261C . . . Inner holding member
261D . . . First inner holding member
261H . . . Distal end side holding member
262, 262C, 262D . . . Outer holding member
262H . . . Proximal end side holding member
263D . . . Second inner holding member
270 . . . Resin member

What is claimed is:

1. A light irradiation device having an elongated outer shape, the light irradiation device comprising:
    an optical fiber configured to emit a light from a distal end of the optical fiber and including a curved part, the curved part orienting the distal end in a direction intersecting with a longitudinal direction of the light irradiation device; and
    a light transmitting holder holding the curved part so as to maintain a shape of the curved part, wherein
    the optical fiber includes a core and an outer surface layer, and
    the holder has a refractive index lower than a refractive index of the outer surface layer of the optical fiber.

2. The light irradiation device according to claim 1, wherein
    the holder is arranged adjacent to an inner peripheral side of the curved part.

3. The light irradiation device according to claim 2, further comprising:
    a hollow shaft accommodating the optical fiber and the holder, wherein
    a proximal end side with respect to the holder within the hollow shaft is filled with a resin member having a refractive index lower than the refractive index of the holder.

4. The light irradiation device according to claim 3, wherein
    a part of the curved part on a distal end side of the curved part protrudes from a distal end of the hollow shaft, and the holder covers a periphery of the part of the curved part protruding from the hollow shaft.

5. The light irradiation device according to claim 1, wherein
the holder includes:
an inner holder arranged adjacent to an inner peripheral side of the curved part, and
an outer holder arranged adjacent to an outer peripheral side of the curved part, and
the outer holder has a refractive index lower than a refractive index of the inner holder.

6. The light irradiation device according to claim 5, wherein
the inner holder includes:
a first inner holder, and
a second inner holder disposed proximally of the first inner holder, and
a refractive index of the second inner holder is lower than a refractive index of the first inner holder and higher than the refractive index of the outer holder.

7. The light irradiation device according to claim 6, further comprising:
a hollow shaft accommodating the optical fiber and the holder, wherein
a proximal end side with respect to the holder within the hollow shaft is filled with a resin member having a refractive index lower than the refractive index of the holder.

8. The light irradiation device according to claim 7, wherein
a part of the curved part on a distal end side of the curved part protrudes from a distal end of the hollow shaft, and
the holder covers a periphery of the part of the curved part protruding from the hollow shaft.

9. The light irradiation device according to claim 5, further comprising:
a hollow shaft accommodating the optical fiber and the holder, wherein
a proximal end side with respect to the holder within the hollow shaft is filled with a resin member having a refractive index lower than the refractive index of the holder.

10. The light irradiation device according to claim 9, wherein
a part of the curved part on a distal end side of the curved part protrudes from a distal end of the hollow shaft, and
the holder covers a periphery of the part of the curved part protruding from the hollow shaft.

11. The light irradiation device according to claim 1, further comprising:
a hollow shaft accommodating the optical fiber and the holder, wherein
a proximal end side with respect to the holder within the hollow shaft is filled with a resin member having a refractive index lower than the refractive index of the holder.

12. The light irradiation device according to claim 11, wherein
a part of the curved part on a distal end side of the curved part protrudes from a distal end of the hollow shaft, and
the holder covers a periphery of the part of the curved part protruding from the hollow shaft.

13. The light irradiation device according to claim 1, further comprising:
a hollow shaft accommodating the optical fiber and the holder, wherein a part of the curved part on a distal end side of the curved part protrudes from a distal end of the hollow shaft, and
the holder covers a periphery of the part of the curved part protruding from the hollow shaft and has an outer diameter that is the same as an outer diameter of the hollow shaft.

14. A light irradiation system comprising:
a light irradiation device having an elongated outer shape, wherein
the light irradiation device includes:
an optical fiber configured to emit a light from a distal end of the optical fiber and including a curved part, the curved part orienting the distal end in a direction intersecting with a longitudinal direction of the light irradiation device; and
a light transmitting holder holding the curved part so as to maintain a shape of the curved part, wherein
the optical fiber includes a core, or the optical fiber includes the core and an outer surface layer, and
the holder has a refractive index lower than a refractive index of the core or a refractive index of the outer surface layer of the optical fiber; and
an elongated tubular catheter configured to receive the light irradiation device, wherein
the catheter includes:
a light transmitting portion configured to transmit light from inside the catheter to outside the catheter, at a position corresponding to the distal end of the optical fiber when the light irradiation device is inserted into the catheter.

15. The light irradiation system according to claim 14, wherein
the holder is arranged adjacent to an inner peripheral side of the curved part.

16. The light irradiation system according to claim 14, wherein
the holder includes:
an inner holder arranged adjacent to an inner peripheral side of the curved part, and
an outer holder arranged adjacent to an outer peripheral side of the curved part, and
the outer holder has a refractive index lower than a refractive index of the inner holder.

17. The light irradiation system according to claim 16, wherein
the inner holder includes:
a first inner holder, and
a second inner holder disposed proximally of the first inner holder, and
a refractive index of the second inner holder is lower than a refractive index of the first inner holder and higher than the refractive index of the outer holder.

18. The light irradiation system according to claim 14, the light irradiation device further comprising:
a hollow shaft accommodating the optical fiber and the holder, wherein
a proximal end side with respect to the holder within the hollow shaft is filled with a resin member having a refractive index lower than the refractive index of the holder.

19. The light irradiation system according to claim 18, wherein
a part of the curved part on a distal end side of the curved part protrudes from a distal end of the hollow shaft, and
the holder covers a periphery of the part of the curved part protruding from the hollow shaft.

20. The light irradiation system according to claim 14, the light irradiation device further comprising:
- a hollow shaft accommodating the optical fiber and the holder, wherein
- a part of the curved part on a distal end side of the curved part protrudes from a distal end of the hollow shaft, and
- the holder covers a periphery of a part of the curved part protruding from the hollow shaft and has an outer diameter that is the same as an outer diameter of the hollow shaft.

* * * * *